US010100060B2

(12) United States Patent
Ben-David et al.

(10) Patent No.: US 10,100,060 B2
(45) Date of Patent: Oct. 16, 2018

(54) ASYMMETRIC SYNTHESIS OF FUNAPIDE

(71) Applicant: Xenon Pharmaceuticals Inc., Burnaby (CA)

(72) Inventors: Ronen Ben-David, Netanya (IL); Jian Chen, Hillsborough, NJ (US); Michael A. Christie, Phoenixville, PA (US); Mina Gadelrab Dimitri, Plainsboro, NJ (US); Graciela Noemi Gershon, Kfar-Saba (IL); Linli He, West Chester, PA (US); Nelson G. Landmesser, Downingtown, PA (US); Daniel V. Levy, Philadelphia, PA (US); Orel Yosef Mizrahi, Elad (IL); Partha S. Mudipalli, Downingtown, PA (US); Harlan F. Reese, Mountain View, CA (US); Joseph A. Sclafani, Malvern, PA (US); Yi Wang, Chester Springs, PA (US)

(73) Assignee: Xenon Pharmaceuticals Inc., Burnaby (CA)

( * ) Notice: Subject to any disclaimer, the term of this patent is extended or adjusted under 35 U.S.C. 154(b) by 0 days.

(21) Appl. No.: 15/625,173

(22) Filed: Jun. 16, 2017

(65) Prior Publication Data

US 2018/0002341 A1 Jan. 4, 2018

Related U.S. Application Data

(60) Provisional application No. 62/351,071, filed on Jun. 16, 2016, provisional application No. 62/427,993, filed on Nov. 30, 2016.

(51) Int. Cl.
*C07D 491/20* (2006.01)
*C07D 405/10* (2006.01)
*C07D 209/34* (2006.01)
*B01J 31/02* (2006.01)

(52) U.S. Cl.
CPC ........ *C07D 491/20* (2013.01); *B01J 31/0204* (2013.01); *B01J 31/0232* (2013.01); *B01J 31/0244* (2013.01); *B01J 31/0245* (2013.01); *B01J 31/0271* (2013.01); *B01J 2231/40* (2013.01); *C07B 2200/13* (2013.01)

(58) Field of Classification Search
CPC ... C07D 491/20; C07D 405/10; C07D 209/34
USPC .......................................... 548/410; 549/344
See application file for complete search history.

(56) References Cited

U.S. PATENT DOCUMENTS

| 3,723,459 | A | 3/1973 | Paragamian |
| 4,886,788 | A | 12/1989 | Skuballa et al. |
| 4,935,446 | A | 6/1990 | Imaki et al. |
| 6,110,969 | A | 8/2000 | Tani et al. |
| 6,225,347 | B1 | 5/2001 | Buchmann et al. |
| 6,235,780 | B1 | 5/2001 | Ohuchida et al. |
| 6,262,293 | B1 | 7/2001 | Tani et al. |
| 6,288,119 | B1 | 9/2001 | Ohuchida et al. |
| 6,355,627 | B1 | 3/2002 | Ishida et al. |
| 7,700,641 | B2 | 4/2010 | Chafeev et al. |
| 7,799,798 | B2 | 9/2010 | Chafeev et al. |
| 7,935,721 | B2 | 5/2011 | Sun et al. |
| 8,101,647 | B2 | 1/2012 | Chafeev et al. |
| 8,106,087 | B2 | 1/2012 | Chafeev et al. |
| 8,263,606 | B2 | 9/2012 | Chafeev et al. |
| 8,415,370 | B2 | 4/2013 | Chafeev et al. |
| 8,445,696 | B2 | 5/2013 | Cadieux et al. |
| 8,450,358 | B2 | 5/2013 | Chafeev et al. |
| 8,466,188 | B2 | 6/2013 | Chafeev et al. |
| 8,742,109 | B2 | 6/2014 | Cadieux et al. |
| 8,883,840 | B2 | 11/2014 | Chafeev et al. |
| 8,916,580 | B2 | 12/2014 | Chafeev et al. |
| 9,260,446 | B2 | 2/2016 | Cadieux et al. |
| 9,458,178 | B2 | 10/2016 | Chafeev et al. |
| 9,480,677 | B2 | 11/2016 | Chafeev et al. |
| 9,487,535 | B2 | 11/2016 | Sun et al. |
| 9,504,671 | B2 | 11/2016 | Winters et al. |
| 9,695,185 | B2 | 7/2017 | Cadieux et al. |
| 2004/0038970 | A1 | 2/2004 | Thurieau et al. |
| 2004/0167224 | A1 | 8/2004 | Ozaki et al. |
| 2007/0049609 | A1 | 3/2007 | Broka et al. |
| 2011/0086899 | A1 | 4/2011 | Winters et al. |
| 2011/0237567 | A9 | 9/2011 | Chafeev et al. |
| 2011/0269788 | A1 | 11/2011 | Cadieux et al. |
| 2011/0294842 | A9 | 12/2011 | Cadieux et al. |
| 2012/0035199 | A9 | 2/2012 | Chafeev et al. |
| 2012/0122909 | A9 | 5/2012 | Chafeev et al. |
| 2013/0274483 | A1* | 10/2013 | Sun ...................... C07D 209/34 548/410 |
| 2017/0066777 | A1 | 3/2017 | Sun et al. |
| 2017/0073351 | A1 | 3/2017 | Chafeev et al. |
| 2017/0095449 | A1 | 4/2017 | Winters et al. |
| 2017/0114075 | A1 | 4/2017 | Chafeev et al. |

FOREIGN PATENT DOCUMENTS

| JP | 7-508976 A | 10/1995 |
| WO | WO 93/23083 A1 | 11/1993 |
| WO | WO 00/42044 A1 | 7/2000 |
| WO | WO 2005/035498 A1 | 4/2005 |
| WO | WO 2005/105753 A2 | 11/2005 |
| WO | WO 2006/110654 A1 | 10/2006 |
| WO | WO 2006/110917 A2 | 10/2006 |
| WO | WO 2007/025925 A1 | 3/2007 |

(Continued)

OTHER PUBLICATIONS

U.S. Appl. No. 15/604,348, filed May 24, 2017, Cadieux et al.
Asano et al., "Asymmetric Catalytic Cycloetherification Mediated by Bifunctional Organocatalysts,"*J. Am. Chem. Soc.* 133: 16711-16713, 2011, with supporting information, 44 pages.

(Continued)

*Primary Examiner* — Matthew P Coughlin
*Assistant Examiner* — Sagar Patel
(74) *Attorney, Agent, or Firm* — Seed IP Law Group LLP

(57) ABSTRACT

This invention is directed to asymmetric synthesis of funapide, which is useful for the treatment and/or prevention of sodium channel-mediated diseases or conditions, such as pain.

18 Claims, 1 Drawing Sheet

(56) References Cited

FOREIGN PATENT DOCUMENTS

| WO | WO 2008/046087 A2 | 4/2008 |
|---|---|---|
| WO | WO 2008/060789 A2 | 5/2008 |
| WO | WO 2008/110741 A2 | 9/2008 |
| WO | WO 2010/045197 A1 | 4/2010 |
| WO | WO 2010/045251 A2 | 4/2010 |
| WO | WO 2011/002708 A1 | 1/2011 |
| WO | WO 2011/047173 A9 | 4/2011 |
| WO | WO 2011/047174 A1 | 4/2011 |
| WO | WO 2011/106729 A2 | 9/2011 |
| WO | WO 2013/154712 A1 | 10/2013 |
| WO | WO 2017/218920 A1 | 12/2017 |

OTHER PUBLICATIONS

Bennett and Xie, "A peripheral mononeuropathy in rat that produces disorders of pain sensation like those seen in man," *Pain* 33: 87-107, 1988.

Corey and Noe, "Preparation of O-Allyl-N-(9-Anthracenylmethyl)Cinchonidinium Bromide as a Phase Transfer Catalyst for the Enantioselective Alkylation of Glycine Benzophenone Imine tert-Butyl Ester: (4S)-2-(Benzhydrylidenamino)Pentanedioic Acid, 1-tert-Butyl Ester-5-Methyl Ester [[Cinchonanium, 1-(9-anthracenylmethyl)-9-(2-propenyloxy)-, bromide, $(8\alpha,9R)$-and L-Glutamic acid, N-(diphenylmethylene)-, 1-(1,1-dimethylethyl) 5-methyl ester]]," *Organic Syntheses* 80(11): 38-45, 2003; Col. vol. 11: 404-409.

Dehmlow et al., "Monodeazacinchona Alkaloid Derivatives: Synthesis and Preliminary Applications as Phase-Transfer Catalysts," *Eur. J. Org. Chem.* 13: 2087-2093, 2002.

Goldberg et al., "Loss-of-function mutations in the $Na_v1.7$ gene underlie congenital indifference to pain in multiple human populations," *Clin. Genet.* 71: 311-319, 2007.

Guillaumet et al., "Synthese d'un analogue dioxinique du psoralene," *Tetrahedron Letters* 29(22): 2665-2666, 1988.

Ikoma et al., "The neurobiology of itch," *Nature Reviews Neuroscience* 7: 535-547, Jul. 2006.

Klugbauer et al., "Structure and functional expression of a new member of the tetrodotoxin-sensitive voltage-activated sodium channel family from human neuroendocrine cells," *EMBO J.* 14(6): 1084-1090, 1995.

Lossin et al., "Molecular Basis of an Inherited Epilepsy," *Neuron* 34: 877-884, Jun. 13, 2002.

MacNicol, "Clathrates and Molecular Inclusion Phenomena," *Chemical Society Reviews* 7(1): 65-87, 1978.

Nicolaou et al., "The Second Total Synthesis of Diazonamide A," *Angew. Chem. Int. Ed.* 42: 1753-1758, 2003.

Ooi and Maruoka, "Recent Advances in Asymmetric Phase-Transfer Catalysis," *Angew. Chem. Int. Ed.* 46: 4222-4266, 2007.

Reddy et al., "Synthesis and Pharmacological Evaluation of N,N-Diarylguanidines as Potent Sodium Channel Blockers and Anticonvulsant Agents," *J. Med. Chem.* 41(17): 3298-3302, 1998.

Saenger, "Cyclodextrin Inclusion Compounds in Research and Industry," *Angew. Chem. Int. Ed. Engl* 19: 344-362, 1980.

Saishin Souyaku-Kagaku, 1st volume, Chapter 21, Yakubutsu no Sayou no Rittai-Kagaku II: Enantiomer, Ken-ichiro Otsuka, Technomics Corporation, 1998, 1st edition, pp. 475-501, 28 pages.

Shin-Jikkenn Kagaku Koza I, Kihon-sosa, 1975, pp. 325-327, 4 pages.

Sircar et al., "Synthesis and SAR of N-Benzoyl-1-Biphenylalanine Dervatives: Discovery of TR-14035, a Dual $\alpha_4\beta_7/\alpha_4\beta_1$ Integrin Antagonist," *Bioorganic & Medicinal Chemistry Letters* 10: 2051-2066, 2002.

Swamy et al., "Mitsunobu and Related Reactions: Advances and Applications," *Chem. Rev.* 109: 2551-2651, 2009.

Vakulya et al., "Highly Enantioselective Conjugate Addition of Nitromethane to Chalcones Using Bifunctional Chinchona Organocatalysts," *Organic Letters* 7(10): 1967-1969, 2005.

Weber and Czugler, "Functional Group Assisted Clathrate Formation—Scissor-Like and Roof-Shaped Host Molecules," *Topics in Current Chemistry* 149: 45-135, 1988.

International Search Report and Written Opinion, dated Oct. 6, 2006, for PCTAN PCT/US2006/014352, 11 pages.

International Search Report and Written Opinion, dated Apr. 1, 2011, for PCTAN PCT/US2010/052704, 12 pages.

International Preliminary Report on Patentability, dated Apr. 17, 2012, for PCTAN PCT/US2010/052704, 6 pages.

Official Action from Intellectual Property Australia, dated Aug. 14, 2015, for Patent Application No. 2010306768, 3 pages.

Response to Official Action from Intellectual Property Australia, dated Jul. 20, 2016, for Patent Application No. 2010306768, 36 pages.

Official Action from Canadian Intellectual Property Office, dated May 27, 2016, for Patent Application No. 2,777,543, 4 pages.

Response to Official Action from Canadian Intellectual Property Office, dated Nov. 28, 2016, for Patent Application No. 2,777,543, 22 pages.

Translation of Official Action from Ministry of Scientific Research Academy of scientific Research & Technology Patent Office, dated Aug. 15, 2014, for Patent Application No. PCT/2012.671, 6 pages.

Translation of Official Action from Ministry of Scientific Research Academy of scientific Research & Technology Patent Office, dated Apr. 22, 2015, for Patent Application No. PCT/2012.671, 7 pages.

Response to Official Action from European Patent Office, dated Dec. 14, 2012, for Patent Application No. 10 771 606.0, 25 pages.

Official Action from European Patent Office re extended European search report, dated Apr. 9, 2014, for Patent Application No. 14000519.0, 9 pages.

Response to Official Action from European Patent Office, dated Apr. 24, 2015, for Patent Application No. 14000519.0, 10 pages.

Official Action from European Patent Office, dated Aug. 4, 2016, for Patent Application No. 14000519.0, 5 pages.

Response to Official Action from European Patent Office, dated Dec. 14, 2016, for Patent Application No. 14000519.0, 4 pages.

Translation of Official Action from Japanese Patent Office, dated Oct. 31, 2014, for Patent Application No. 2012-534362, 6 pages.

Translation of Official Action from Japanese Patent Office, dated Oct. 15, 2015, for Patent Application No. 2015-039888, 5 pages.

Official Action from New Zealand Intellectual Property Office, dated Dec. 6, 2012, for Patent Application No. 599334, 2 pages.

Official Action from New Zealand Intellectual Property Office, dated Mar. 13, 2014, for Patent Application No. 622072, 2 pages.

Response to Official Action from New Zealand Intellectual Property Office, dated Jun. 9, 2015, for Patent Application No. 622072, 22 pages.

Official Action from New Zealand Intellectual Property Office, dated Jun. 22, 2015, for Patent Application No. 622072, 2 pages.

Official Action from New Zealand Intellectual Property Office, dated Oct. 5, 2015, for Patent Application No. 712378, 2 pages.

Translation of Official Action from Intellectual Property Office of Russia, dated Jul. 14, 2014, for Patent Application No. 2012119550, 2 pages.

Official Action from Intellectual Property Office of Singapore, dated Aug. 14, 2014, for Patent Application No. 2012025391, 14 pages.

Cadieux et al., entitled Synthetic Methods for Spiro-Oxindole Compounds, Restriction Requirement dated May 7, 2012, for U.S. Appl. No. 12/904,880, 7 pages.

Cadieux et al., entitled Synthetic Methods for Spiro-Oxindole Compounds, Response to Restriction Requirement dated Jun. 7, 2012, for U.S. Appl. No. 12/904,880, 1 page.

Cadieux et al., entitled Synthetic Methods for Spiro-Oxindole Compounds, Office Action dated Aug. 16, 2012, for U.S. Appl. No. 12/904,880, 40 pages.

Cadieux et al., entitled Synthetic Methods for Spiro-Oxindole Compounds, Amendment dated Nov. 16, 2012, for U.S. Appl. No. 12/904,880, 15 pages.

Cadieux et al., entitled Synthetic Methods for Spiro-Oxindole Compounds, Notice of Allowance dated Jan. 24, 2013, for U.S. Appl. No. 12/904,880, 11 pages.

(56) References Cited

OTHER PUBLICATIONS

Cadieux et al., entitled Synthetic Methods for Spiro-Oxindole Compounds, Preliminary Amendment dated Jul. 22, 2014, for U.S. Appl. No. 14/272,297, 5 pages.
Cadieux et al., entitled Synthetic Methods for Spiro-Oxindole Compounds, Office Action dated Mar. 11, 2015, for U.S. Appl. No. 14/272,297, 48 pages.
Cadieux et al., entitled Synthetic Methods for Spiro-Oxindole Compounds, Amendment dated Jun. 29, 2015, for U.S. Appl. No. 14/272,297, 11 pages.
Cadieux et al., entitled Synthetic Methods for Spiro-Oxindole Compounds, Preliminary Amendment dated Jul. 21, 2016, for U.S. Appl. No. 14/989,600, 4 pages.
Cadieux et al., entitled Synthetic Methods for Spiro-Oxindole Compounds, Office Action dated Sep. 27, 2016, for U.S. Appl. No. 14/989,600, 54 pages.
Cadieux et al., entitled Synthetic Methods for Spiro-Oxindole Compounds, Amenment dated Dec. 27, 2016, for U.S. Appl. No. 14/989,600, 5 pages.
Cadieux et al., entitled Synthetic Methods for Spiro-Oxindole Compounds, Office Action dated Feb. 1, 2013, for U.S. Appl. No. 13/620,391, 42 pages.
Cadieux et al., entitled Synthetic Methods for Spiro-Oxindole Compounds, Amendment dated May 1, 2013, for U.S. Appl. No. 13/620,391, 7 pages.
Cadieux et al., entitled Synthetic Methods for Spiro-Oxindole Compounds, Office Action dated Jul. 31, 2013, for U.S. Appl. No. 13/620,391, 6 pages.
Cadieux et al., entitled Synthetic Methods for Spiro-Oxindole Compounds, Amendment dated Oct. 31, 2013, for U.S. Appl. No. 13/620,391, 8 pages.
Cadieux et al., entitled Synthetic Methods for Spiro-Oxindole Compounds, Notice of Allowance dated Jan. 22, 2014, for U.S. Appl. No. 13/620,391, 12 pages.
International Search Report and Written Opinion, dated Oct. 1, 2010, for PCTAN PCT/US2010/040187, 13 pages.
International Search Report and Written Opinion, dated Jun. 9, 2011, for PCTAN PCT/US2011/026359, 14 pages.
International Preliminary Report on Patentability, dated Nov. 1, 2012, for PCTAN PCT/US2011/026359, 10 pages.
Translation of Official Action from Korean Intellectual Property Office, dated Apr. 17, 2016, for United Arab Emirates Patent Application No. P/0905/2012, 12 pages.
Official Action from Intellectual Property Australia, dated Sep. 30, 2015, for Patent Application No. 2011220396, 3 pages.
Translation of Official Action from State Intellectual Property Office of China, dated Sep. 18, 2013, for Patent Application No. 201180010245.7, 7 pages.
Translation of Official Action from State Intellectual Property Office of China, dated Jul. 17, 2014, for Patent Application No. 201180010245.7, 6 pages.
Translation of Official Action from State Intellectual Property Office of China, dated Mar. 18, 2015, for Patent Application No. 201180010245.7, 7 pages.
Official Action from European Patent Office, dated Jul. 19, 2013, for Patent Application No. 11 707 750.3, 7 pages.
Translation of Official Action from Patent Office of Japan, dated Jan. 27, 2015, for Patent Application No. 2012-555199, 4 pages.
Translation of Official Action from Patent Office of Japan, dated Dec. 22, 2015, for Patent Application No. 2012-555199, 6 pages.
Official Action from Intellectual Property Office of New Zealand, dated May 7, 2013, for New Zealand Patent Application No. 601667, 2 pages.
Response to Official Action from Intellectual Property Office of New Zealand, dated Jul. 30, 2014, for Patent Application No. 601667, 55 pages.
Official Action from Intellectual Property Office of New Zealand, dated Aug. 12, 2014, for New Zealand Patent Application No. 601667, 2 pages.

Translation of Official Action from Patent Office of Russia, dated Feb. 19, 2015, for Patent Application No. 2012140955, 4 pages.
Official Action from Intellectual Property Office of Singapore, dated Jul. 11, 2014, for Singapore Patent Application No. 2012056909, 13 pages.
Winters et al., entitled Pharmaceutical Compositions of Spiro-Oxindole Compound for Topical Administration and Their Use as Therapeutic Agents, Preliminary Amendment dated Oct. 30, 2012, for U.S. Appl. No. 13/580,129, 7 pages.
Winters et al., entitled Pharmaceutical Compositions of Spiro-Oxindole Compound for Topical Administration and Their Use as Therapeutic Agents, Restriction Requirement dated Nov. 19, 2013, for U.S. Appl. No. 13/580,129, 7 pages.
Winters et al., entitled Pharmaceutical Compositions of Spiro-Oxindole Compound for Topical Administration and Their Use as Therapeutic Agents, Response to Requirement for Unity of Invention dated Feb. 19, 2014, for U.S. Appl. No. 13/580,129, 3 pages.
Winters et al., entitled Pharmaceutical Compositions of Spiro-Oxindole Compound for Topical Administration and Their Use as Therapeutic Agents, Office Action dated May 7, 2014, for U.S. Appl. No. 13/580,129, 52 pages.
Winters et al., entitled Pharmaceutical Compositions of Spiro-Oxindole Compound for Topical Administration and Their Use as Therapeutic Agents, Amendment dated Aug. 7, 2014, for U.S. Appl. No. 13/580,129, 10 pages.
Winters et al., entitled Pharmaceutical Compositions of Spiro-Oxindole Compound for Topical Administration and Their Use as Therapeutic Agents, Office Action dated Oct. 31, 2014, for U.S. Appl. No. 13/580,129, 16 pages.
Winters et al., entitled Pharmaceutical Compositions of Spiro-Oxindole Compound for Topical Administration and Their Use as Therapeutic Agents, Amendment dated Feb. 2, 2015, for U.S. Appl. No. 13/580,129, 8 pages.
Winters et al., entitled Pharmaceutical Compositions of Spiro-Oxindole Compound for Topical Administration and Their Use as Therapeutic Agents, Office Action dated Apr. 6, 2015, for U.S. Appl. No. 13/580,129, 14 pages.
Winters et al., entitled Pharmaceutical Compositions of Spiro-Oxindole Compound for Topical Administration and Their Use as Therapeutic Agents, Amendment dated Oct. 6, 2015, for U.S. Appl. No. 13/580,129, 8 pages.
Winters et al., entitled Pharmaceutical Compositions of Spiro-Oxindole Compound for Topical Administration and Their Use as Therapeutic Agents, Office Action dated Jan. 15, 2016, for U.S. Appl. No. 13/580,129, 11 pages.
Winters et al., entitled Pharmaceutical Compositions of Spiro-Oxindole Compound for Topical Administration and Their Use as Therapeutic Agents, Amendment dated Jul. 13, 2016, for U.S. Appl. No. 13/580,129, 9 pages.
Winters et al., entitled Pharmaceutical Compositions of Spiro-Oxindole Compound for Topical Administration and Their Use as Therapeutic Agents, Amendment dated Sep. 28, 2016, for U.S. Appl. No. 13/580,129, 5 pages.
International Search Report and Written Opinion, dated Jun. 28, 2013, for PCTAN PCT/US2013/030219, 17 pages.
Invitation to Pay Additional Fees, dated May 3, 2013, for PCTAN PCT/US2013/030219, 5 pages.
International Preliminary Report on Patentability, dated Oct. 14, 2014, for PCTAN PCT/US2013/030219, 10 pages.
Official Action from Intellectual Property Australia, dated Nov. 21, 2016, for Patent Application No. 2013246485, 3 pages.
Translation of Official Action from Eurasian Patent Office, dated Sep. 29, 2015, for Patent Application No. 201491854/28, 5 pages.
Translation of Official Action from Eurasian Patent Organization, dated Jun. 26, 2017, for Patent Application No. 201491854/28, 4 pages.
Translation of Official Action from State Intellectual Property Office of China, dated Sep. 21, 2015, for Patent Application No. 201380030552.0, 13 pages.
Official Action from European Patent Office, dated Jan. 27, 2015, for Patent Application No. 13710961.7, 2 pages.
Response to Official Action from European Patent Office, dated Aug. 5, 2015, for Patent Application No. 13710961.7, 8 pages.

(56) References Cited

OTHER PUBLICATIONS

Official Action from European Patent Office, dated Nov. 21, 2016, for Patent Application No. 13710961.7, 6 pages.
Response to Official Action from European Patent Office, dated Apr. 3, 2017, for Patent Application No. 13710961.7, 73 pages.
Translation of Official Action from Israel Patent Office dated Jul. 7, 2016, for Patent Application No. 235006, 4 pages.
Translation of Official Action from Israel Patent Office dated Sep. 27, 2016, for Patent Application No. 235006, 3 pages.
Response to Official Action from Israel Patent Office dated Dec. 7, 2016, for Patent Application No. 235006, 165 pages.
Translation of Official Action from Japanese Patent Office dated Sep. 8, 2016, for Patent Application No. 2015-505723, 7 pages.
Translation of Official Action from Japanese Patent Office dated Apr. 24, 2017, for Patent Application No. 2015-505723, 3 pages.
Official Action from Intellectual Property Office of New Zealand, dated Jul. 9, 2015, for Patent Application No. 630189, 2 pages.
Official Action from New Zealand Intellectual Property Office, dated Feb. 1, 2017, for Patent Application No. 630189, 4 pages.
Official Action from Intellectual Property Office of New Zealand dated Feb. 1, 2017, for Patent Application No. 727889, 5 pages.
International Search Report and Written Opinion, dated Oct. 26, 2017, for PCTAN PCT/US2017/037921, 16 pages.

* cited by examiner

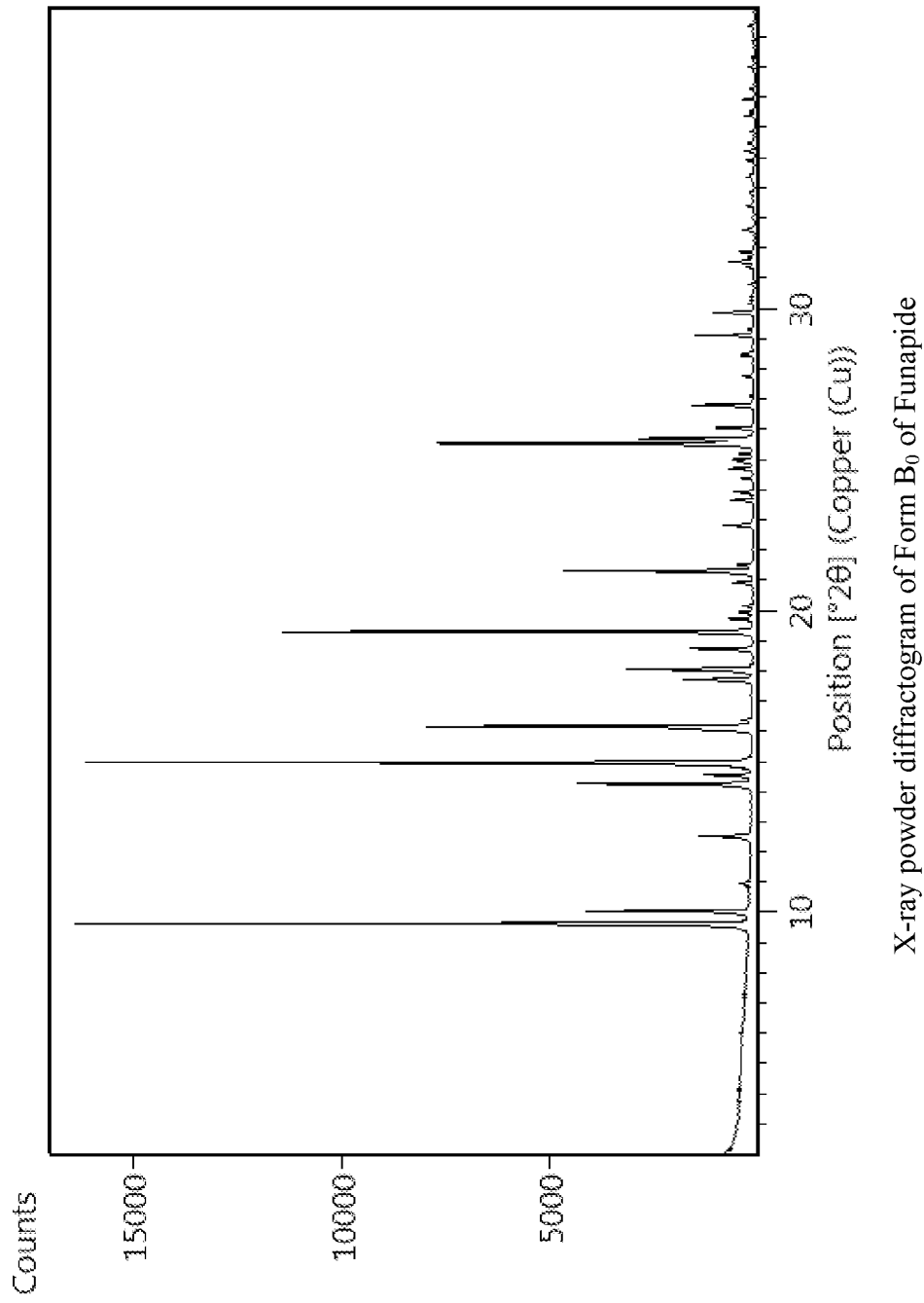

ASYMMETRIC SYNTHESIS OF FUNAPIDE

FIELD OF THE INVENTION

The present invention is directed to improved methods of preparing funapide as well as various intermediates involved therein. In particular, this invention is directed to an asymmetric synthesis of funapide, which is useful in treating sodium channel-mediated diseases or conditions, such as pain, as well as other diseases and conditions associated with the mediation of sodium channels, particularly diseases and conditions associated with the activity of sodium channel $Na_V1.7$.

BACKGROUND OF THE INVENTION

Sodium channels play a diverse set of roles in maintaining normal and pathological states, including the long-recognized role that voltage-gated sodium channels play in the generation of abnormal neuronal activity and neuropathic or pathological pain. Damage to peripheral nerves following trauma or disease can result in changes to sodium channel activity and the development of abnormal afferent activity including ectopic discharges from axotomised afferents and spontaneous activity of sensitized intact nociceptors. These changes can produce long-lasting abnormal hypersensitivity to normally innocuous stimuli, or allodynia. Examples of neuropathic pain include, but are not limited to, post-herpetic neuralgia, trigeminal neuralgia, diabetic neuropathy, chronic lower back pain, phantom limb pain, and pain resulting from cancer and chemotherapy, chronic pelvic pain, complex regional pain syndrome and related neuralgias.

PCT Published Patent Application No. WO 2006/110917, PCT Published Patent Application No. WO 2010/045251, PCT Published Patent Application No. WO 2010/045197, PCT Published Patent Application No. WO 2011/047174, PCT Published Patent Application No. WO 2011/002708 and PCT Published Patent Application No. WO 2013/154712 disclose certain spiro-oxindole compounds which are useful as voltage-gated sodium channel inhibitors and therefore useful in treating diseases and conditions which are associated with voltage-gated sodium channel activity, particularly the activity of sodium channel $Na_V1.7$.

One of these spiro-oxindole compounds is funapide, which is also known as TV-45070 or XEN402. Funapide has the following structure:

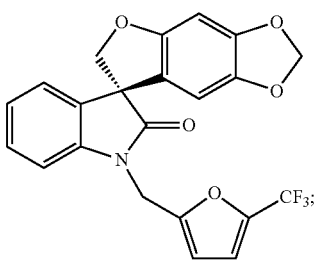

and a chemical name of (S)-1'-{[5-(trifluoromethyl)furan-2-yl]methyl}spiro[furo[2,3-f][1,3]benzodioxole-7,3'-indol]-2'(1'H)-one. Funapide is specifically disclosed in PCT Published Patent Application No. WO 2011/002708, which corresponds to U.S. Pat. No. 8,450,358, the disclosure of which is incorporated in full herein by reference.

Methods of preparing funapide and/or its racemate are disclosed, for example, in PCT Published Patent Application No. WO 2006/110917, PCT Published Patent Application No. WO 2011/047174 and PCT Published Patent Application No. WO 2013/154712. In particular, PCT Published Patent Application No. WO 2011/047174 discloses a method of preparing funapide by resolving its racemate by either SMB chromatography or by chiral HPLC and WO 2013/154712 discloses methods of preparing funapide by asymmetric synthesis.

There exists, therefore, a need for additional methods of preparing funapide which result in increased yields and purity of funapide than the methods previously disclosed.

SUMMARY OF THE INVENTION

In one aspect, this invention is directed to methods of preparing funapide, which has the following formula:

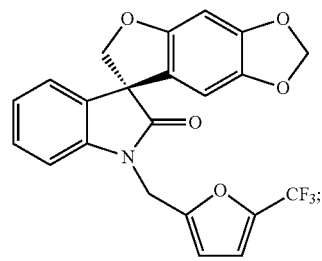 [SMILES: O=C1N(Cc2ccc(C(F)(F)F)o2)c2ccccc2[C@]12COc1cc3c(cc12)OCO3]

as the isolated (S)-enantiomer substantially free from the corresponding (R)-enantiomer, or as a non-racemic mixture of enantiomers having an enantiomeric excess of the (S)-enantiomer over the corresponding (R)-enantiomer of greater than 94%, more preferably greater than 98%, or most preferably greater than 99%, wherein the methods employ a coupling step in the absence of a Grignard reagent, an asymmetric carbon-carbon bond formation step utilizing a catalyst, and an intramolecular cyclization step which avoids the use of certain Mitsunobu reaction reagents. The disclosed methods provide increased yields of funapide from the starting materials and reagents and also provide increased purity of funapide in the final product from the previously disclosed methods.

In particular, this invention is directed to methods of preparing funapide having the following formula:

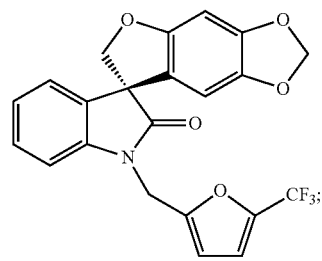 [SMILES: O=C1N(Cc2ccc(C(F)(F)F)o2)c2ccccc2[C@]12COc1cc3c(cc12)OCO3]

as the isolated (S)-enantiomer substantially free from the corresponding (R)-enantiomer, or as a non-racemic mixture of enantiomers having an enantiomeric excess of the (S)-enantiomer over the corresponding (R)-enantiomer of greater than 94%;

wherein the method comprises treating a compound of formula (G):

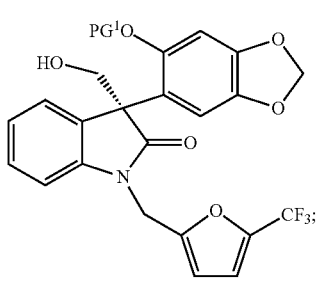

where PG¹ is an oxygen-protecting group, as an isolated (S)-enantiomer or a non-racemic mixture of enantiomers having an enantiomeric excess of the (S)-enantiomer over the corresponding (R)-enantiomer of greater than 94%, under suitable deprotection and intramolecular cyclization conditions to provide funapide, as described above.

In another aspect, this invention is directed to a method of preparing funapide having the following formula:

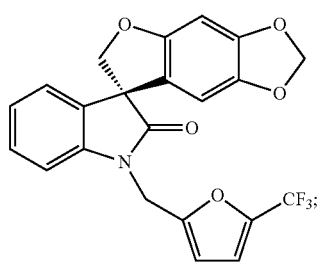 [SMILES: O=C1N(Cc2ccc(C(F)(F)F)o2)c2ccccc2[C@]12COc1cc3c(cc12)OCO3]

as the isolated (S)-enantiomer substantially free from the corresponding (R)-enantiomer, or as a non-racemic mixture of enantiomers having an enantiomeric excess of the (S)-enantiomer over the corresponding (R)-enantiomer of greater than 94%;

wherein the method comprises:
(1) a coupling step comprising:
  (a) treating a compound of formula (A):

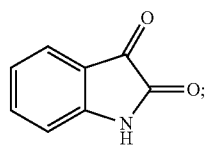

with a compound of formula (B):

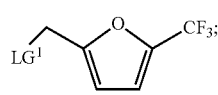

where LG¹ is a leaving group, under suitable N-alkylation conditions to form a reaction mixture, and (b) adding to the reaction mixture a compound of formula (C):

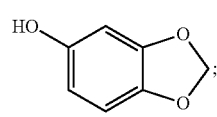

under suitable coupling conditions to provide a compound of formula (D):

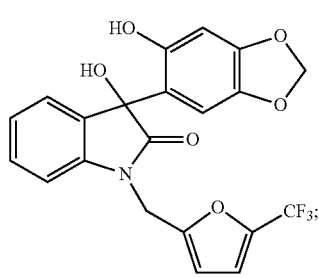

which is isolated from the reaction mixture by standard isolation techniques;

(2) a dehydroxylation step comprising treating the compound of formula (D) under suitable dehydroxylation conditions to provide a compound of formula (E):

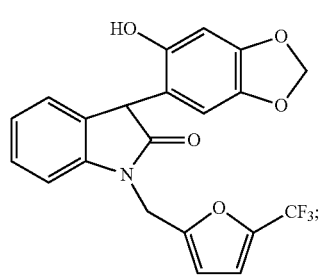

(3) an oxygen-protecting step comprising treating the compound of formula (E) with a compound of formula PG¹X, where X is bromo, chloro or iodo and PG¹ is an oxygen-protecting group under suitable protecting conditions to provide a compound of formula (F):

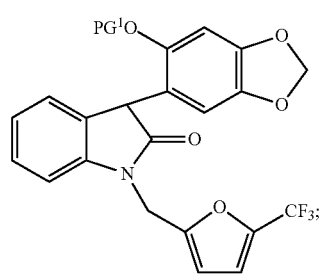

where PG¹ is an oxygen-protecting group;
(4) a C—C bond formation step comprising treating the compound of formula (F) with formaldehyde in the presence of a catalyst under suitable C—C bond formation conditions to provide a compound of formula (G):

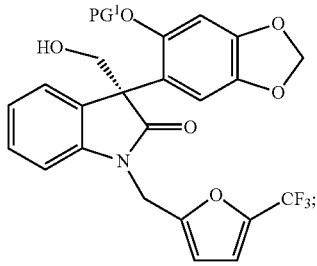
(G)

where PG$^1$ is an oxygen-protecting group, as an isolated (S)-enantiomer or a non-racemic mixture of enantiomers having an enantiomeric excess of the (S)-enantiomer over the corresponding (R)-enantiomer of greater than 94%;

(5) an intramolecular cyclization step comprising treating the compound of formula (G), as an isolated (S)-enantiomer or a non-racemic mixture of enantiomers having an enantiomeric excess of the (S)-enantiomer over the corresponding (R)-enantiomer of greater than 94%, under suitable intramolecular cyclization conditions to provide funapide, as an isolated (S)-enantiomer or a non-racemic mixture of enantiomers having an enantiomeric excess of the (S)-enantiomer over the corresponding (R)-enantiomer of greater than 94%;

(6) optionally, a purification step comprising treating funapide under suitable purification conditions to provide a higher yield of funapide than achieved in step (6) above.

In an embodiment of the above aspect, the compound of formula (Ga):

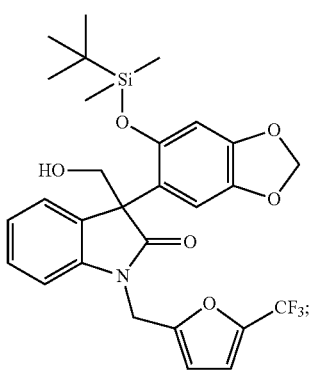
(Ga)

formed in the preparation of formula (G) in step (4) above, is optionally treated under suitable retro-aldol reaction conditions to form a compound of formula (F), as described above, which can then be used in step (4) above.

In another aspect, this invention is directed to novel intermediates prepared and/or utilized in the methods disclosed herein.

In another aspect, this invention is directed to a catalyst utilized in the methods disclosed herein, wherein the catalyst is a compound of formula (H):

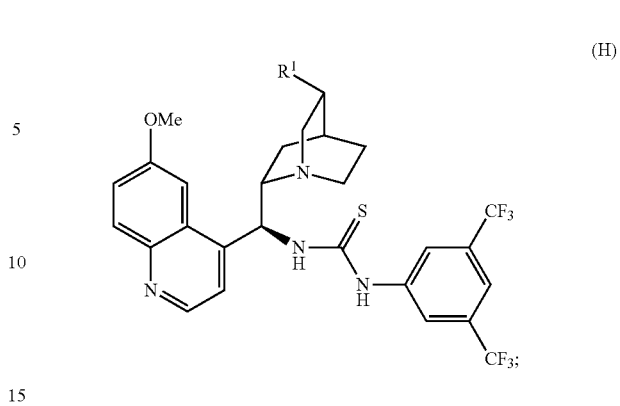
(H)

where R$^1$ is R$^1$ is —CH$_2$—CH$_3$ or —CH=CH$_2$.

In another aspect, this invention is directed to methods for the preparation of catalysts utilized in the methods disclosed herein.

These aspects of the invention and others are described in more detail below.

BRIEF DESCRIPTION OF THE DRAWINGS

FIG. 1 shows an X-ray powder diffractogram of Form B$_0$ of funapide.

DETAILED DESCRIPTION OF THE INVENTION

Definitions

As used in the specification and appended claims, unless specified to the contrary, the following terms have the meaning indicated:

"Enantiomeric excess" or "ee" refers to a product wherein one enantiomer is present in excess of the other, and is defined as the absolute difference in the mole fraction of each enantiomer. Enantiomeric excess is typically expressed as a percentage of an enantiomer present in a mixture relative to the other enantiomer. For purposes of this invention, a compound prepared by the methods disclosed herein may exist as an isolated (S)-enantiomer or a non-racemic mixture where the (S)-enantiomer is present in enantiomeric excess of greater than 94%, preferably greater than 98% and most preferably greater than 99% of the corresponding (R)-enantiomer.

The chemical naming protocol and structure diagrams used herein are a modified form of the I.U.P.A.C. nomenclature system. For complex chemical names employed herein, a substituent group is named before the group to which it attaches. For example, cyclopropylethyl comprises an ethyl backbone with cyclopropyl substituent. In the chemical structure diagrams herein all bonds are identified, except for some carbon atoms, which are assumed to be bonded to sufficient hydrogen atoms to complete the valency. Stereochemistry is designated herein through the use of the conventional solid wedge bonds and dashed wedge bonds, i.e., a solid wedge bond indicates that the bond is above the plane of the paper and a dashed wedge bond indicates that the bond is below the plane of the paper. Non-wedge bonds are intended to include all possible stereochemical configurations.

Thus, for example, funapide is depicted herein as:

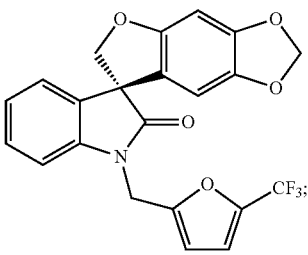 [SMILES: O=C1N(Cc2ccc(C(F)(F)F)o2)c2ccccc2[C@]12COc1cc3c(cc12)OCO3]

and is named herein as (S)-1'-{[5-(trifluoromethyl)furan-2-yl]methyl}spiro[furo[2,3-f][1,3]benzodioxole-7,3'-indol]-2'(1'H)-one or as TV-45070.

"(S)-enantiomer" refers to the (S)-enantiomer of the following compound:

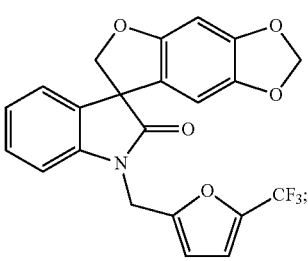

(I)

which has the chemical name of 1'-{[5-(trifluoromethyl)furan-2-yl]methyl}spiro[furo[2,3-f][1,3]benzodioxole-7,3'-indol]-2'(1'H)-one and which may be referred to herein as the "racemate." The racemate is disclosed and claimed in PCT Published Patent Application No. WO 2006/110917 and U.S. Pat. No. 7,700,641, the disclosure of which is incorporated in full by reference herein. Funapide is the (S)-enantiomer of 1'-{[5-(trifluoromethyl)furan-2-yl]methyl}spiro[furo[2,3-f][1,3]benzodioxole-7,3'-indol]-2'(1'H)-one and has the structure shown above for funapide.

"(R)-enantiomer" refers to the (R)-enantiomer of 1'-{[5-(trifluoromethyl)furan-2-yl]methyl}spiro[furo[2,3-f][1,3]benzodioxole-7,3'-indol]-2'(1'H)-one, as shown above, and has the following structure:

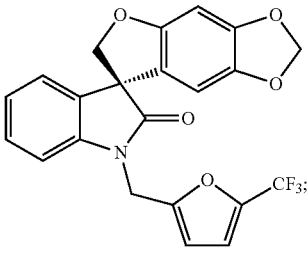 [SMILES: O=C1N(Cc2ccc(C(F)(F)F)o2)c2ccccc2[C@@]12COc1cc3c(cc12)OCO3]

and the chemical name of (R)-1'-{[5-(trifluoromethyl)furan-2-yl]methyl}spiro[furo[2,3-f][1,3]benzodioxole-7,3'-indol]-2'(1'H)-one.

When a reaction mixture or solution is characterized herein as being at or allowed to come to "room temperature" (often abbreviated as "RT") or "ambient temperature", it is intended to mean that the temperature of the mixture or solution is close to, or the same as, that of the space, e.g., the room or fume hood, in which the mixture or solution is located. Typically, room temperature is from about 20° C. to about 30° C., or about 22° C. to about 27° C., or about 25° C.

The amount of solvent employed in a chemical process, e.g., a reaction or a crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval for the process or step that spans the time during the night when that process or step may not be actively observed. This time interval is from about 8 to about 20 hours, or about 10-18 hours, typically about 16 hours. A process or step may be referred to herein as being carried out "over the weekend." This refers to a time interval for the process or step that spans the time from the end of the last day of a regular work week to the beginning of the first day of the regular work week. The time interval is from about 48 to about 72 hours, typically about 64 hours, plus or minus 8 hours.

As used herein, the term "reduced pressure" refers to a pressure that is less than atmospheric pressure. For example, reduced pressure is about 10 mbar to about 50 mbar.

LIST OF ABBREVIATIONS

The following abbreviations may also be used herein:
A % refers to area percentage by HPLC or GC.
AcOH refers to acetic acid.
DI refers to deionized.
DIAD refers to diisopropyl azodicarboxylate.
DMF refers to N,N-dimethylformamide.
DPPA refers to diphenylphosphoryl azide.
Et$_3$SiH refers to triethylsilane.
GC refers to gas chromatography.
HPLC refers to high-performance liquid chromatography.
IPA refers to isopropanol.
IPC refers to in-process control testing of a particular step in the synthesis of funapide.
KF refers to Karl-Fischer coulometric titration method to determine residual water content.
LOD refers to loss on drying.
NaOAc refers to sodium acetate.
NMR refers to nuclear magnetic resonance.
MeOH refers to methanol.
Ph$_2$PCl refers to chlorodiphenylphosphine.
Ph$_3$P refers to triphenylphosphine.
(PhO)$_2$P(O)N$_3$ refers to diphenylphosphorylazide.
SMB refers to simulated moving bed.
TBDMS refers to tert-butyldimethylsilyl.
TBDMS-Cl refers to tert-butyldimethylsilyl chloride.
TFA refers to trifluoroacetic acid.
TGA refers to thermogravimetric analysis.
THF refers to tetrahydrofuran.
TLC refers to thin layer chromatography.

EMBODIMENTS OF THE INVENTION

As noted above in the Summary of the Invention, one aspect of the invention is a method of preparing funapide having the following formula:

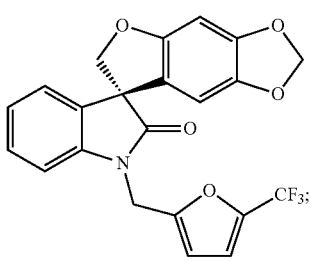 [SMILES: O=C1N(Cc2ccc(C(F)(F)F)o2)c2ccccc2[C@]12COc1cc3c(cc12)OCO3]

as the isolated (S)-enantiomer substantially free from the corresponding (R)-enantiomer, or as a non-racemic mixture of enantiomers having an enantiomeric excess of the (S)-enantiomer over the corresponding (R)-enantiomer of greater than 94%;
wherein the method comprises treating a compound of formula (G):

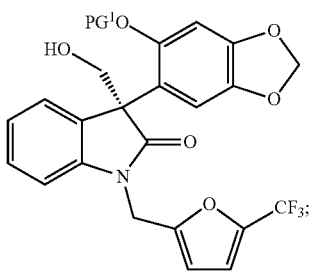

where $PG^1$ is an oxygen-protecting group, as an isolated (S)-enantiomer or a non-racemic mixture of enantiomers having an enantiomeric excess of the (S)-enantiomer over the corresponding (R)-enantiomer of greater than 94%, under suitable deprotection and intramolecular cyclization conditions to provide funapide, as described above.

Of this aspect, one embodiment is wherein the suitable intramolecular cyclization conditions comprise the use of a phosphine reagent.

Of this embodiment, a further embodiment is wherein the compound of formula (G) is treated to the suitable intramolecular cyclization conditions in the absence of an azodicarboxylate ester.

Of this embodiment, another further embodiment is wherein the phosphine reagent is chlorodiphenylphosphine.

Of this aspect, another embodiment is wherein the suitable deprotection conditions comprise treating the compound of formula (G) in a polar aprotic solvent with an aqueous acid solution.

Of this aspect, another embodiment further comprises a C—C bond formation step prior to treating a compound of formula (G) under suitable intra-molecular cyclization conditions, wherein the C—C bond formation step comprises treating a compound of formula (F):

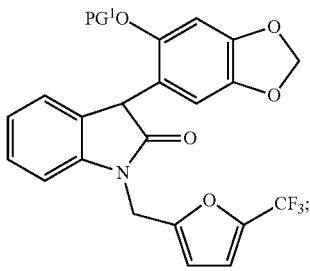

where $PG^1$ is as defined above for the compounds of formula (G), with formaldehyde in the presence of a catalyst under suitable C—C bond formation conditions to provide the compound of formula (G), as an isolated (S)-enantiomer or a non-racemic mixture of enantiomers having an enantiomeric excess of the (S)-enantiomer over the corresponding (R)-enantiomer of greater than 94%, as described above.

Of this embodiment, another embodiment is wherein the catalyst is a thiourea-substituted quinine or hydroquinine derivative.

Of this another embodiment, a further embodiment is wherein the catalyst is a compound of formula (H):

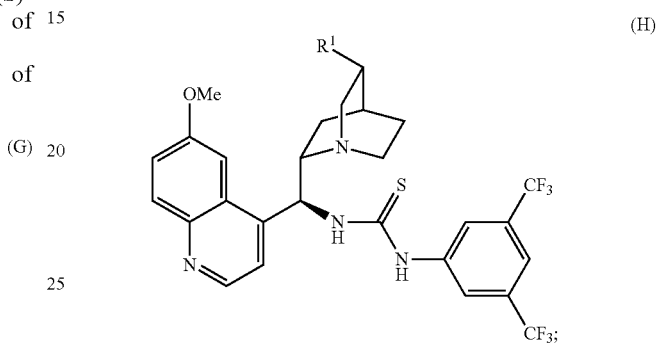

wherein $R^1$ is —$CH_2$—$CH_3$ or —CH=$CH_2$.

Of this another embodiment, a further embodiment is wherein the suitable C—C bond formation conditions comprise suspending the compound of formula (F) in an organic solvent and combining the suspension of the compound of formula (F) with an inorganic base.

Of this another embodiment, a further embodiment comprises an optional retro-aldol reaction step prior to treating the compound of formula (F) under suitable C—C bond formation conditions, wherein the retro-aldol reaction step comprises treating a compound of formula (Ga):

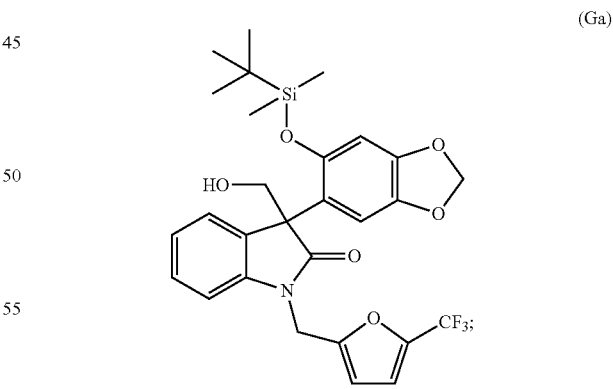

under suitable retro-aldol reaction conditions to provide a compound of formula (F), as described above.

Of this another embodiment, another further embodiment comprises an oxygen-protecting step prior to treating the compound of formula (F) under suitable C—C bond formation conditions, wherein the oxygen-protecting step comprises treating a compound of formula (E):

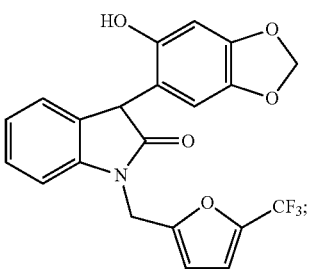

(E)

with a compound of formula PG¹X, where X is bromo, chloro or iodo and PG¹ is an oxygen-protecting group under suitable oxygen-protecting conditions to provide a compound of formula (F), as described above.

Of this further embodiment, another embodiment is wherein the suitable protecting conditions comprise treating the compound of formula (E) with an oxygen-protecting group provider in an polar aprotic solvent in the presence of a base.

Of this further embodiment, another further embodiment comprises a dehydroxylation step prior to treating the compound of formula (E) under suitable C—C bond formation conditions, wherein the dehydroxylation step comprises treating a compound of formula (D):

(D)

under suitable dehydroxylation conditions to provide a compound of formula (E), as described above.

Of this further embodiment, an embodiment is wherein the suitable dehydroxylation conditions comprise dehydroxylation of the compound of formula (D) in the presence of a strong acid.

Of this further embodiment, another embodiment comprises a coupling step prior to treating a compound of formula (D) under suitable dehydroxylation conditions, wherein the coupling step comprises:
(a) treating a compound of formula (A):

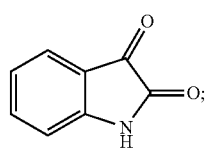

(A)

with a compound of formula (B):

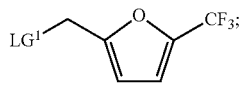

(B)

wherein LG¹ is a leaving group, under suitable N-alkylation conditions to form a reaction mixture, and (b) adding to the reaction mixture a compound of formula (C):

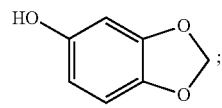

(C)

under suitable coupling conditions to provide a compound of formula (D), as described above.

Of this embodiment, a further embodiment is wherein the compound of formula (D) is isolated from the reaction mixture by crystallization under suitable crystallization conditions.

Of this embodiment, another further embodiment is wherein the suitable N-alkylation conditions comprise reductive amination conditions in the presence of an aldehyde and a reducing agent.

Of this embodiment, another further embodiment is wherein the suitable coupling conditions comprise treating the compound of formula (C) with the reaction mixture to form the compound of formula (D) in the absence of a Grignard reagent.

One embodiment of the invention are intermediates prepared and/or utilized in the methods disclosed herein. Such intermediates include, but are not limited to, compounds of formula (F) and (G), as shown below:

(F)

and (G)

where PG¹ is an oxygen protecting group, such as benzyl, alkyl, tert-butyldiphenylsilyl, triphenylsilyl or tert-butyldimethylsilyl.

Another embodiment of the invention is a catalyst which is a compound of formula (H):

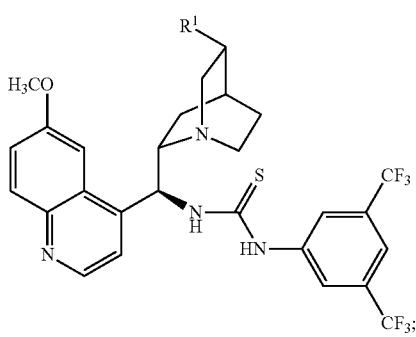

(H)

where R[1] is —CH$_2$—CH$_3$ or —CH=CH$_2$.

Another embodiment of the invention is a method of preparing a catalyst which is a compound of formula (H):

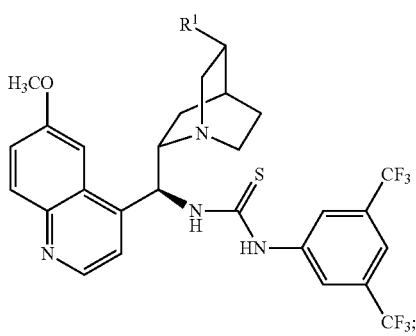

(H)

wherein R[1] is —CH=CH$_2$ or —CH$_2$—CH$_3$, wherein the method comprises treating a compound of formula (L):

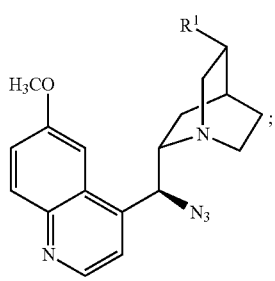

(L)

wherein R[1] is —CH=CH$_2$ or —CH$_2$—CH$_3$, with a compound of formula (M):

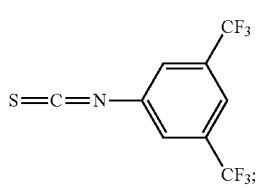

(M)

under suitable Mitsunobu reaction conditions to form the compound of formula (H), which is isolated under suitable conditions followed by recrystallization.

In one embodiment of this embodiment, the compound of formula (H) prepared is a compound of formula (Ha):

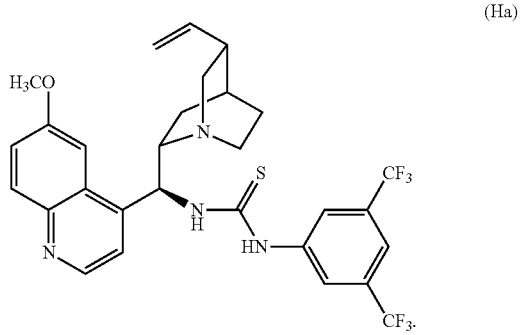 [SMILES: C=CC1CN2CCC1CC2[C@@H](NC(=S)Nc1cc(C(F)(F)F)cc(C(F)(F)F)c1)c1ccnc2ccc(OC)cc12]

(Ha)

In another embodiment of this embodiment, the compound of formula (H) prepared is a compound of formula (Hb):

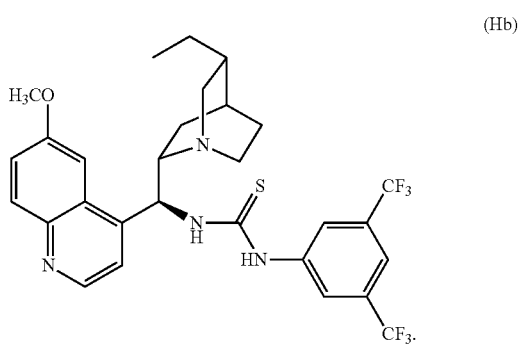 [SMILES: CCC1CN2CCC1CC2[C@@H](NC(=S)Nc1cc(C(F)(F)F)cc(C(F)(F)F)c1)c1ccnc2ccc(OC)cc12]

(Hb)

In another embodiment of the invention, the compound of formula (Ga):

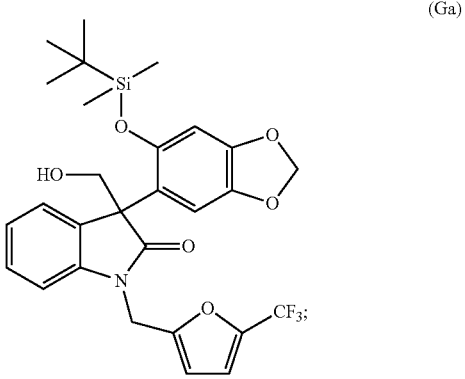 [SMILES: CC(C)(C)[Si](C)(C)Oc1cc2c(cc1C1(CO)C(=O)N(Cc3ccc(C(F)(F)F)o3)c3ccccc31)OCO2]

(Ga)

formed in the preparation of formula (G), is treated under suitable retro-aldol reaction conditions to form a compound of formula (F), as described above.

Specific embodiments of the methods of the invention, including the suitable conditions for each of the above described steps, are described in more detail below in the Methods of the Invention and the Examples.

Methods of the Invention

The methods of the invention are directed to asymmetric syntheses of funapide having an enantiomeric excess of the (S)-enantiomer over the corresponding (R)-enantiomer of greater than 94%, more preferably greater than 98%, or most preferably greater than 99%.

In general, the starting compounds and reagents utilized in the methods may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Smith, M. B., *March's Advanced Organic Chemistry: Reactions*, Mechanisms, and Structure, 7th edition (Wiley, December 2013)) or prepared as described herein or in PCT Published Patent Application No. WO 2006/110917, PCT Published Patent Application No. WO 2010/45251, PCT Published Patent Application No. WO 2010/045197, PCT Published Patent Application No. WO 2011/047174 and PCT Published Patent Application No. WO 2011/002708.

As used herein, the term "leaving group" has the standard definition, i.e., an atom (or a group of atoms) that is displaced during a heterolytic bond cleavage as a stable species taking with it the bonding electrons. Examples of such leaving groups include halogen, such as bromo, chloro and iodo, and mesylate and tosylate.

As used herein "suitable coupling conditions" generally refers to reaction conditions which allow for carbon-carbon bond formation without the use of a Grignard reagent and which is promoted by an acid, base or metal.

As used herein "suitable oxygen-protecting conditions" generally refers to reaction conditions which allow for the covalent bonding of an oxygen-protecting group to an oxygen atom in order to prevent subsequent reactions of reagents with the oxygen. "Suitable oxygen-protecting conditions" are further described herein in the description of Reaction Scheme 1 and are further described in detail in Greene, T. W. and Wuts, P. G. M. *Greene's Protective Groups in Organic Synthesis* (2006), 4$^{th}$ Ed. Wiley. Suitable oxygen-protecting groups for an oxygen atom ("oxygen-protecting groups") include, but are not limited to, trialkylsilyl or diarylalkylsilyl (e.g., tert-butyldimethylsilyl, tert-butyldiphenylsilyl or trimethylsilyl), tetrahydropyranyl, benzyl, and the like. Preferably, a suitable oxygen-protecting group is tert-butyldimethylsilyl.

"Suitable deprotection conditions" as used herein generally refers to reaction conditions which allow for the simple cleavage of a protecting group. Suitable deprotection conditions include, but are not limited to, treating the protected compound in a polar aprotic solvent with an aqueous acid solution. "Suitable deprotection conditions" are further described herein in the description of Reaction Scheme 1 and are further described in detail in Greene, T. W. and Wuts, P. G. M. *Greene's Protective Groups in Organic Synthesis* (2006), 4$^{th}$ Ed. Wiley.

"Suitable crystallization conditions" as used herein generally refers to reaction conditions which allow for the crystallization process of forming a solid (i.e., a crystal or an amorphous solid) from a solution. "Suitable crystallization conditions" also refers to reaction conditions whereby a mass transfer of a solute from the liquid solution to a solid crystalline phase occurs. Suitable crystals are obtained through a variation of the solubility conditions of the solute in the solvent, including, but not limited to, ethanol, ethyl acetate, tetrahydrofuran or diethyl ether. Mixtures of solvents can also be used in which the solute is dissolved in a solvent in which there is high solubility followed by the addition of an anti-solvent in which the solute is less soluble but impurities are soluble, leading to the formation of a crystalline solid phase. Crystallization may also be induced by the addition of seed crystals of previously crystallized material to a solution containing the same solute. These seed crystals serve as nucleation sites upon which further crystallization takes place, speeding up the process of forming a solid crystalline phase. "Suitable recrystallization conditions" are further described herein in the description of Reaction Scheme 1 and are described in further detail in Mersmann, A., *Crystallization Technology Handbook* (2001), CRC; 2nd ed.

"Suitable carbon-carbon bond formation conditions" or "suitable C—C bond formation conditions" as used herein generally refers to reaction conditions which allow for: a) the transfer of an optionally substituted alkyl group (or substituent) from one molecule to another to form a carbon-carbon bond or b) the condensation with an electrophile which does not contain a leaving group. For example, an intermediate in the Reaction Scheme 1 illustrated below may be treated with an alkylating agent, such as, but not limited to, a benzyl halide, in the presence of a base, such as, but not limited to, sodium methoxide, to yield a product wherein a carbon-carbon bond is formed. C—C bond formation reactions can be carried out under conditions in which one or more substrates are dissolved in a solvent, typically an organic solvent such as, but not limited to, toluene, ethyl acetate, dioxane, or diethyl ether, and combined with an inorganic base such as, but not limited to, lithium hydroxide, sodium hydroxide, potassium hydroxide, potassium phosphate, sodium bicarbonate, cesium carbonate, or potassium carbonate. The base can be used as a solid or be dissolved in water to form a solution or slurry. A catalyst may be used to accelerate C—C bond formation in the absence of base though hydrogen-bonding interactions in both partners. This catalyst may also impart a stereochemical preference in the newly formed bond. In one embodiment of the invention, the catalyst used in the C—C bond formation described herein is a thiourea-substituted hydroquinine derivative. In another embodiment of the invention, the catalyst is a quinine or hydroquinine derivative. C—C bond formation conditions are further described herein in the description of Reaction Scheme 1 and the following Examples and are also described in further detail in Smith, M. B., *March's Advanced Organic Chemistry: Reactions*, Mechanisms, and Structure, 7th edition (Wiley, December 2013).

"Suitable retro-aldol reaction conditions" as used herein generally refers to reaction conditions which allow for the cleavage of a β-hydroxycarbonyl compound into two carbonyl containing compounds. In general, suitable retro-aldol reaction conditions refer to conditions wherein the β-hydroxycarbonyl compound in a solvent, such as, but not limited to isopropanol, toluene, methanol, isopropyl acetate and heptane, is treated with OH$^-$ or an organic base, such as triethylamine or 1,4-diazabicyclo[2.2.2]octane (DABCO) in the optional presence of a aldehyde scavenger, such as 2-imidazolidone, aqueous ammonia or urea, which can be added to the mixture to shift the reaction equilibrium to completion.

"Filtering aid" as used herein refers to a substance which enhances the filtration of a substance by enabling the filtrate to pass through a filter at a greater flow rate than if the filtering aid were not used by filtering very fine particles that would otherwise pass through or dog the filter paper. Examples of such filtering aids are diatomaceous earth, perlite and cellulose.

"Catalyst" as used herein generally refers to thiourea-substituted hydroquinine derivatives or thiourea-substituted quinine derivatives. Additional examples include quaternary ammonium salts of quinidine, quinine, cinchonine or cinchonidine. Such derivatives are commercially available or can be prepared by methods known to one skilled in the art.

In one embodiment of the invention, the catalyst is a quinine derivative of the following formula (Ha):

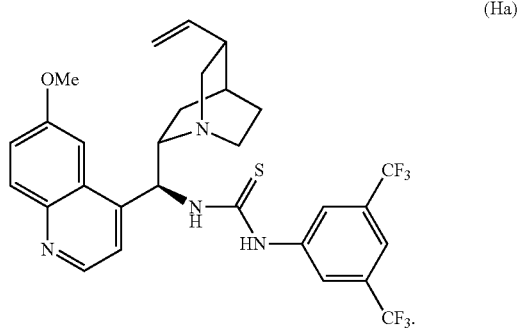 [SMILES: C=CC1CN2CCC1CC2[C@@H](NC(=S)Nc1cc(C(F)(F)F)cc(C(F)(F)F)c1)c1ccnc2ccc(OC)cc12]

(Ha)

The compound of formula (Ha) is commercially available, for example, from Sigma-Aldrich, or can be prepared by methods known to one skilled in the art. Alternatively, the compound of formula (Ha) can be prepared by the method disclosed herein. The method disclosed herein for the preparation of the compound of formula (Ha), which is an embodiment of the invention, is a scalable process (i.e., producing kilograms of the catalyst) with a relatively high yield (greater than 50%) and a desirable purity of the catalyst (greater than 93% A).

In another embodiment of the invention, the catalyst is a hydroquinine derivative of the following formula (Hb):

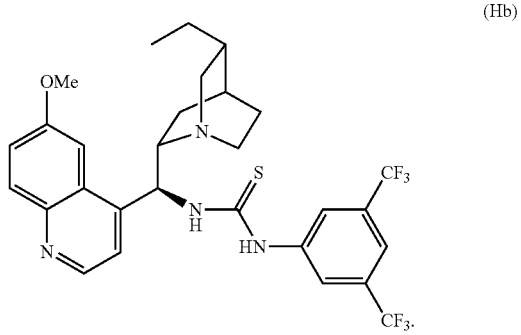 [SMILES: CCC1CN2CCC1CC2[C@@H](NC(=S)Nc1cc(C(F)(F)F)cc(C(F)(F)F)c1)c1ccnc2ccc(OC)cc12]

(Hb)

The compound of formula (Hb) is also commercially available, for example, from Sigma-Aldrich, or can be prepared by methods known to one skilled in the art or by the method disclosed herein. The method disclosed herein for the preparation of the compound of formula (Hb), which is an embodiment of the invention, is a scalable process (i.e., producing kilograms of the catalyst) with a relatively high yield (greater than 50%) and a desirable purity of the catalyst (greater than 95% A).

The methods disclosed herein for the preparation of the compound of formula (Ha) and the compound of formula (Hb) are significantly superior for large scale production than the method previously disclosed in Vakulya, B., Varga, S., Csámpai, A., and Soós, T., Org. Lett. 2005, 7, 1967-1969, for the preparation of the compound of formula (Hb). In particular, the previous method consisted of a three step transformation including a Mitsunobu reaction, a reduction step and a coupling step with an isothiocyanate. Two chromatographic purifications were required in the previous method for the purifications of the intermediate amine and the final product in order to obtain the desired purity. Although the previous method provided gram-scale amounts of the desired product, i.e., the compound of formula (Hb), the method was not feasible for scale-up production of kilogram amounts. In contrast, the methods disclosed herein represent robust and scalable processes which consist of three chemical reaction steps and one recrystallization purification step, all of which can be performed in a single pot until final isolation, thereby significantly improving practicability and productivity.

"Suitable dehydroxylation conditions" as used herein generally refers to reaction conditions which allow for the dehydroxylation of an alcohol, preferably a secondary alcohol, in the presence of a strong acid, such as, but not limited to, trifluoroacetic acid or sulphuric acid. "Suitable dehydroxylation conditions" are further described herein in the description of Reaction Scheme 1 and the following Examples and are also described in further detail in Smith, M. B., March's Advanced Organic Chemistry: Reactions, Mechanisms, and Structure, 7th edition (Wiley, December 2013).

"Suitable N-alkylation conditions" as used herein generally refers to reaction conditions which allow for the alkylation of the relevant nitrogen. Such reaction conditions include the standard conditions of reductive amination in the presence of an aldehyde and a reducing agent, such as, but not limited to, sodium borohydride and may also include alkylation of the nitrogen using a base, such as, but not limited to, potassium carbonate, and an alkylating agent, such as, but not limited to, a benzyl halide. "Suitable N-alkylation conditions" are further described herein in the description of Reaction Scheme 1 and the following Examples and are also described in further detail in Greene, T. W. and P. G. M. Wuts, Greene's Protective Groups in Organic Synthesis (2006), 4th Ed., Wiley.

"Suitable intramolecular cyclization conditions" as used herein generally refers to reaction conditions which allow for the formation of a carbon-oxygen (C—O) bond by the condensation of an acidic component with an alcohol (either primary, secondary or benzyl alcohol) in the presence of triphenylphosphine or another suitable phosphine in order to form a ring. Alternatively, a suitable leaving group may be utilized, to allow for intramolecular formation of a carbon-oxygen (C—O) bond by the corresponding phenol nucleophile. Suitable intramolecular cyclization conditions as used herein do not include the use of an azodicarboxylate ester as used in standard Mitsunobu reactions.

During the processes described herein, in process control (IPC) testing for purity of the desired product was conducted at various stages. Such testing includes, but was not limited to, HPLC, NMR and thermogravimetric analysis (TGA).

As noted above, methods of preparing funapide by resolving the racemate by either SMB chromatography or by chiral HPLC are disclosed in PCT Published Patent Application No. WO 2011/047174. The methods disclosed in PCT Published Patent Application No. WO 2011/047174 do not represent a foundation for a commercial process of preparing funapide due to, inter alia:

1. The need for plug chromatography after the final alkylation to remove colored by-products from the previous step.
2. The fact that over 50% of the material lost in the simulated moving bed (SMB) chromatography stage was the (R)-enantiomer as well as significant cost and solvent waste associated with the SMB separation.
3. The need for installation of the trifluoromethylfuran moiety to facilitate solubility in the SMB chromatography eluent.
4. The potential for genotoxic impurities to carry over in the final isolation.

The advantages of the asymmetric syntheses of funapide as described herein over the syntheses disclosed in PCT Published Patent Application No. WO 2011/047174 and PCT Published Patent Application No. WO 2013/154712 are as follows:

1. The asymmetric syntheses disclosed herein do not require SMB chromatography technology for resolving the racemate of funapide, thereby eliminating a costly step.
2. Chirality is introduced in the compound at an earlier step, thereby eliminating undesirable intermediates and final products, such as the (R)-enantiomer and the racemate.
3. Overall yield of funapide is higher for the syntheses disclosed herein than for the published syntheses.

4. The use of the moisture- and air-sensitive Grignard reagent is avoided.
5. The use of a phosphine reagent without the standard azodicarboxylate ester of the Mitsunobu reaction promotes the intramolecular cyclization without loss of stereochemical integrity and provides a cleaner (less impure) product going into final purification.
6. The use of finely powdered potassium carbonate as a higher yielding alternative to the larger molecular weight cesium salt.
7. Introduction of 2-(bromomethyl)-5-(trifluoromethyl) furan (a compound of formula (B) where $LG^1$ is bromo) occurs early in the synthesis to prevent contamination of downstream products with the compound of formula (B), a known genotoxic agent.
8. The racemate of the compound of formula (G), i.e., the compound of formula (Ga), which is a by-product of the preparation of the compound of formula (G), can optionally be recovered and used to prepare the compound of formula (F), thereby allowing for the recycling of a by-product back into the synthesis.

In addition, the methods disclosed herein for the preparation of the catalysts utilized in the methods of preparing funapide as disclosed herein offer the advantage of providing kilogram amounts of the catalysts with the desired yield and purity and are easily scalable for commercial production.

Funapide, as described above, can be prepared by the method described below in Reaction Scheme 1 where $PG^1$ is an oxygen protecting group, such as benzyl, alkyl, tert-butyldiphenylsilyl, triphenylsilyl or tert-butyldimethylsilyl and $LG^1$ is a leaving group, such as bromo, chloro, iodo, mesylate and tosylate.

REACTION SCHEME 1

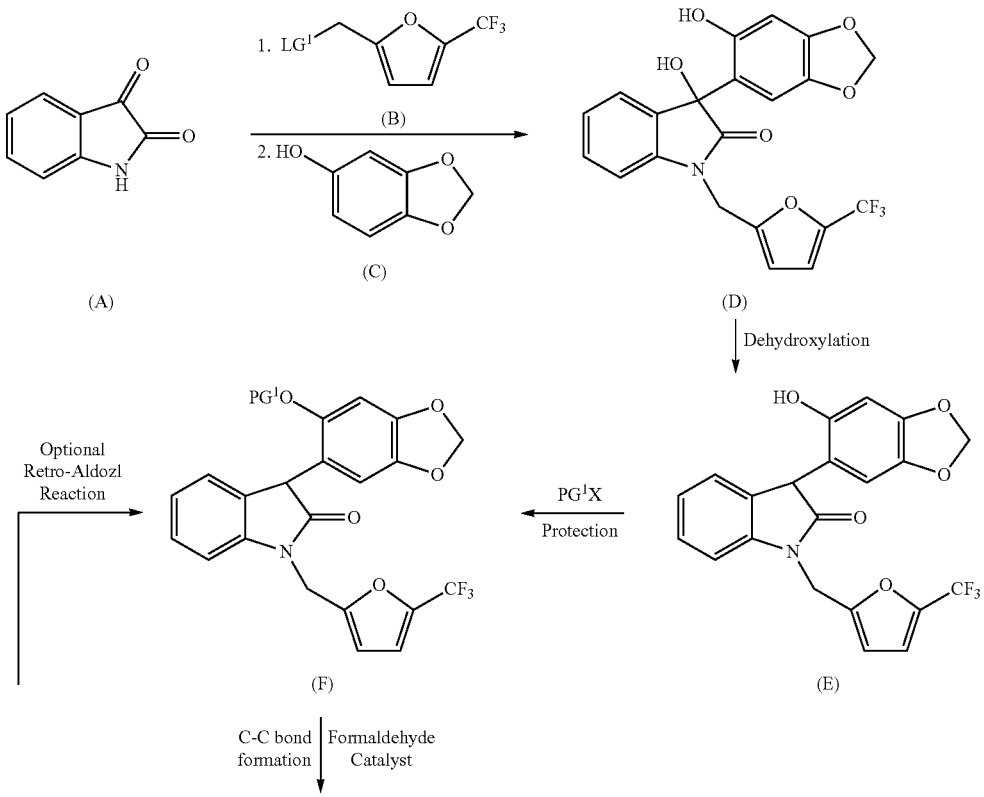

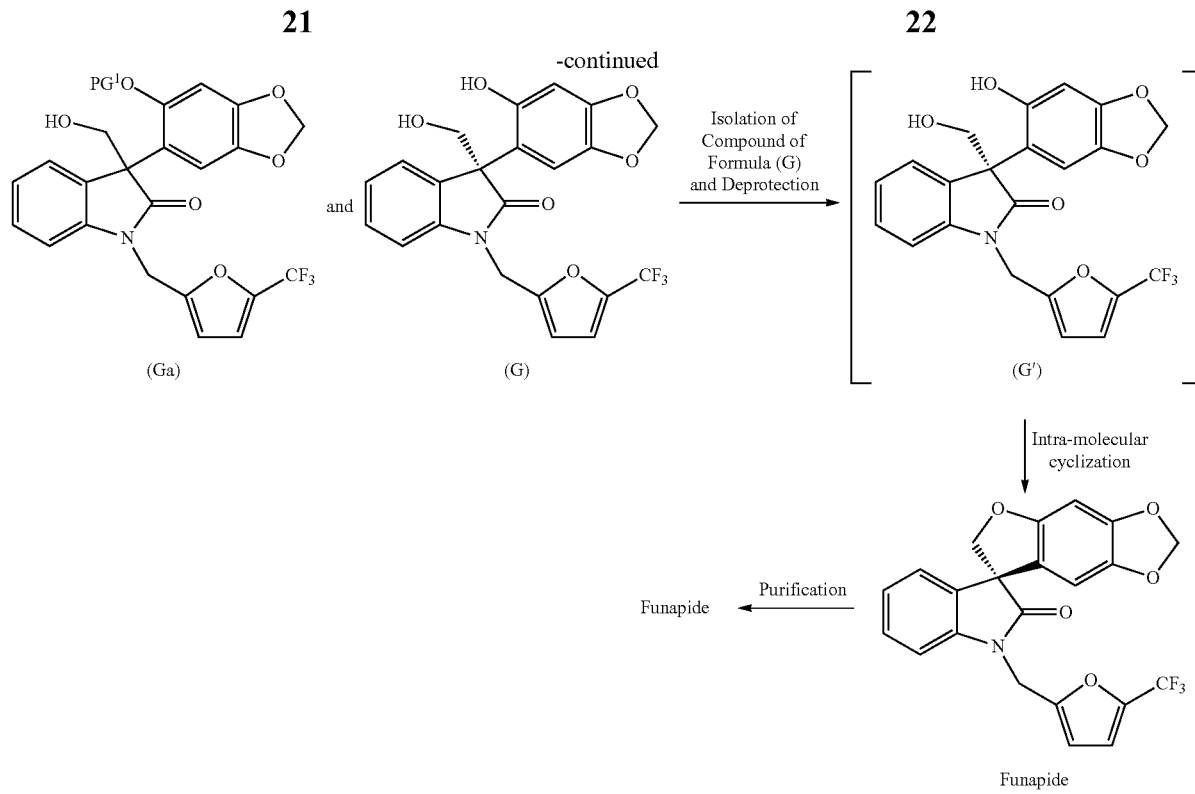

Compounds of formula (A), (B), (C) and PG$^1$X are commercially available or can be prepared according to methods known to one skilled in the art or by the methods disclosed in PCT Published Patent Application No. WO 2006/110917, PCT Published Patent Application No. WO 2010/45251, PCT Published Patent Application No. WO 2010/045197, PCT Published Patent Application No. WO 2011/047174, PCT Published Patent Application No. WO 2011/002708 and PCT Published Patent Application No. WO 2013/154712. The catalysts used in the process are commercially available or prepared according to methods known to one skilled in the art or by the methods disclosed herein.

The asymmetric route set forth above in Reaction Scheme 1 benefits from identical key raw materials, but alters the order of the stages, as disclosed in PCT Published Patent Application No. WO 2011/047174 and PCT Published Patent Application No. WO 2013/154712, in order to enhance selectivity in the asymmetric aldol step, i.e., the C—C bond formation step from compound of formula (F) to compound of formula (G). Thus, installation of 2-(bromomethyl)-5-(trifluoromethyl)furan (a compound of formula (B)) occurs early in the synthesis to avoid alkylation of the phenol and to prevent contamination of downstream products with the compound of formula (B), a known genotoxic agent when LG$^1$ is bromo. Finely powdered potassium carbonate proved to be a successful alternative to the higher molecular weight cesium salt used in PCT Published Patent Application No. WO 2011/047174 in the N-alkylation of isatin (compound of formula (A) with 2-(bromomethyl)-5-(trifluoromethyl)furan (a compound of formula (B)). Potassium carbonate was also shown to promote the coupling of sesamol (compound of formula (C)), thus avoiding the need for the moisture and air-sensitive Grignard reagent as used in PCT Published Patent Application No. WO 2013/154712 and improving the yield over the use of cesium salt.

In addition, in the transformation of the compound of formula (D) to form the compound of formula (E), the amount of trifluoroacetic acid used in the known syntheses was successfully reduced by using methylene chloride as the solvent. Due to the insolubility of both the starting material and the product, dimeric impurities were avoided. Protection of the phenol in the subsequent step enhances the enantiomeric excess of the asymmetric installation of formaldehyde to give the quaternary chiral center. The enantiomeric excess produced in the aldol step is relatively high (greater than 60%) considering the mild reaction temperature and size of the electrophile. However, successful crystallization of the compound of formula (G) from the reaction mixture allowed for the remaining mother liquors to be enriched to greater than 98% ee of the desired (S)-enantiomer.

In addition, by functionalizing the oxindole with the methyl(trifluoromethyl)furan, only one equivalent of formaldehyde is transferred to the compound of formula (E) thus simplifying the intramolecular cyclization. Although the necessary protection of the phenol added an additional step to the synthesis, the deprotection was found to be successfully telescoped in the penultimate stage. The use of chlorodiphenylphosphine, which is commercially available, without the use of the standard azodicarboxylate ester Mitsunobu reagent promoted the intramolecular cyclization of the compound of formula (G) to form funapide without loss of stereochemical integrity while providing a cleaner reaction stream going into the crystallization. Although producing very pure material (>99% relative to impurities) upon crystallization from methanol directly from the reaction mixture, an additional step can be optionally added to remove trace amounts of impurities which may form colored degradants in the formulation, which is described in more detail in the Examples below.

In general, funapide is prepared by the process disclosed above in Reaction Scheme 1 by first treating isatin, the compound of formula (A), with 2-(bromomethyl)-5-(trifluoromethyl)furan, a compound of formula (B), under suitable N-alkylation conditions, for example, in a polar aprotic solvent, such as acetonitrile, DMF, THF, dioxane or dimethoxyethane, in the presence of a base, such as cesium carbonate, anhydrous potassium carbonate, sodium hydride, or calcium hydride. The compound of formula (A) and the base, for example, anhydrous potassium carbonate, were charged to a reactor along with the polar aprotic solvent, for example, DMF, and the resulting slurry was heated to a temperature of between 30° C. and 50° C., for example, at about 48° C., before the compound of formula (B) was added over a period of time from about 1 hour to about 1.5 hours to the reaction mixture and the temperature of the reaction mixture was kept at a temperature of between 40° C. and 55° C. during the addition. The reaction mixture was then cooled to a temperature of between 25° C. and 35° C., for example, to about 30° C. and sesamol, the compound of formula (C) was then added to the reaction mixture over a period of time from about 1 hour to 2 hours, for example, over 80 minutes. The resulting reaction mixture was then stirred for a period of time from about 2.75 hours to 3.25 hours, for example, for about 3.0 hours at a temperature of between 25° C. and 35° C., for example, at about 30° C. The reaction mixture was cooled to ambient temperature, for example, to about 22° C., with or without filtering off any undesired by-product inorganic salts. Crystallization of the desired product, the compound of formula (D), from the filtrate was achieved through suitable crystallization conditions, such as from a solid-free solution of DMF and an appropriate alcohol such as isopropanol at a temperature of from about 45° C. to about 55° C., for example, at about 50° C., to which water, for example, DI water, was added, followed by the addition of seed crystals of the compound of formula (D). Additional water was added over a period of time from about 1 hour to about 2 hours, for example, for about 1.5 hours, and then the reaction mixture was allowed to cool to ambient temperature, for example, to about 22° C. The material may be recrystallized if needed using ethyl acetate and heptane.

Alternatively, prior to the addition of sesamol (compound of formula (C)) to the reaction mixture, the product of the reaction between the compound of formula (A) and the compound of formula (B), i.e., the compound of formula (A') as shown below:

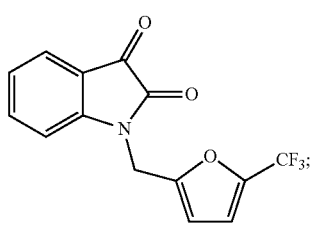

(A')

may be isolated from the reaction mixture by standard techniques, such as by precipitation and filtration. The compound of formula (A') so isolated can then be dissolved in an appropriate polar aprotic solvent and then treated with sesamol as described above to yield the compound of formula (D).

Alternatively, upon completion of the sesamol coupling, isopropanol was added to the reaction mixture and the reaction mixture heated to a temperature of between about 50° C. and 55° C., for example, to about 53° C., for a period of time of between about 20 minutes and 30 minutes, for example, for about 23 minutes. Water, for example, DI water, was added to the reaction mixture over a period of time from about 50 minutes to an hour, for example, over about 54 minutes, while the temperature of the reaction mixture was maintained at a temperature from about 50° C. and 55° C., for example, at about 53° C. Seed crystals of compound of formula (D) were added to the reaction mixture and the reaction mixture stirred for a period of time from about 10 minutes to an hour, for example, for about 30 minutes. The reaction mixture was allowed to cool to a temperature of between about 35° C. and 45° C., for example, to about 40° C. The pH of the reaction mixture was adjusted to a range of 7-9 by adding an appropriate acid, such as acetic acid (1 equivalent) in water, to the reaction mixture over a period of time from about 1 hour to about 2 hours, for example, over about 89 minutes while the temperature was maintained during this period from about 40° C. to about 45° C., for example, to between 41° C. and 44° C. The reaction mixture was allowed to cool to ambient temperature, for example, to about 20° C., over a period of time from about 1 hour to 16 hours. The resulting solids were collected by filtration to yield the compound of formula (D).

Alternatively, the compound of formula (A) and an excess molar equivalent amount of a base, for example, powdered anhydrous potassium carbonate, were charged to a reactor along with a polar aprotic solvent, for example, DMF, and the resulting slurry was heated to a temperature of between 30° C. and 50° C., for example, to about 45° C. A slight excess molar equivalent amount of a compound of formula (B) where $LG^1$ is bromo was added to the reaction mixture over a period of time from about 0.5 hour to about 3.5 hours to keep the temperature of the reaction mixture between 40° C. and 55° C. When the reaction was completed, the reaction mixture may be cooled to a temperature of between 5° C. and 15° C. to confirm completion, and then heated to a temperature of between 20° C. and 40° C., for example, to 30° C. A solution of a slight excess molar equivalent amount of the compound of formula (C) in a polar aprotic solvent, such as DMF, was added to the reaction mixture over a period of time from about 10 minutes to about 3 hours to keep the temperature between 20° C. and 40° C., for example, at between 28° C. and 30° C. The resulting reaction mixture was stirred at a temperature of between 20° C. and 40° C., for example, at about 30° C., for more than 2 hours, for example, for about 3 hours, to complete the reaction. An appropriate amount of an alcohol, such as isopropanol or methanol, was added to the reaction mixture and the reaction mixture was heated to a temperature to a temperature of between 45° C. and 55° C., for example, to about 53° C., for a period of time of between 10 minutes and 1 hour, for example, for about 20-23 minutes. Water, for example, DI water, was then added to the reaction mixture over a period of time of between 30 minutes and 1.5 hours, for example, over about 50-55 minutes, while keeping the temperature of the reaction mixture at between 35° C. and 55° C., for example, at between 53° C. and 55° C. A slurry of seed crystals of compound of formula (D) was added to the reaction mixture and the resulting mixture agitated for a period of time of between 20 minutes and 5 hour, for example, for about 30 minutes. The reaction mixture was allowed to cool to a temperature of between 35° C. and 45° C., for example, to about 40° C. The pH of the reaction mixture was adjusted to a range of 8-9 by adding an appropriate acid, such as acetic acid (1 equivalent) in water, to the reaction mixture over a period of time of between 1 hour to 2 hours, for example, over about 90 minutes, while keeping the temperature of the reaction mixture between 35° C. and 50° C., for example, at between 41° C. and 44° C. The reaction mixture was cooled to a temperature of between 15° C. and 25° C., for example, to above 20° C., over a period of time of between 30 minutes and 1.5 hours, for example, over about 1 hour, to crystallize the desired product. The reaction mixture was kept at a temperature of between 15° C. and 25° C. for more than an hour for example, at about 20° C., overnight. The resulting solids were collected by filtration to yield the compound of formula (D).

Alternatively, upon completion of the sesamol coupling, water, for example, DI water was added to the reaction mixture. The pH of the reaction mixture was adjusted to a range of 8-9 by adding an appropriate acid, such as acetic acid following with addition of ethyl acetate. The compound of formula (D) was isolated from the reaction mixture by organic extraction, repeated washing, distillation and precipitation from ethyl acetate/heptane solvent mixture. The solid was collected by filtration.

The compound of formula (D) so formed was then subjected to suitable dehydroxylation conditions to provide a compound of formula (E). In particular, to the compound of formula (D) was added methylene chloride and the resulting slurry was cooled to a temperature of about 0° C.±5° C., over a period of time, for example, over about 16 minutes. An excess molar equivalent amount of silane or siloxane, for example triethylsilane, was added to the reaction mixture over a period of time, for example, over about 2 minutes, while the temperature was maintained at a temperature of about 0° C.±5° C. An excess molar equivalent amount of a strong mineral or organic acid, for example, hydrochloric acid, trifluoroacetic acid or sulfuric acid, was added to the reaction mixture over a period of time from about 30 minutes to 2 hours, for example, for about 1.0 hour, while the temperature of the reaction mixture was maintained at less than 10° C. The reaction mixture was then heated to a temperature of between about 20° C. and about 30° C., for example, to about 25° C.±3° C., for a period of time from about 30 minutes to about two hours, for example, for about an hour. The compound of formula (E) was isolated from the reaction mixture by organic extraction, repeated washing, distillation with a solvent exchange into heptane, and filtration. Alternatively, after distillation, the compound of formula (E) may be isolated at about 0° C. from solvent mixture of heptane/isopropanol. The material may be recrystallized if needed using isopropanol/heptane solvent mixture.

The compound of formula (E) so formed was then subjected to suitable oxygen-protecting conditions to provide a compound of formula (F). In particular, a mixture of the compound of formula (E) and an excess molar equivalent amount of an oxygen-protecting group provider, for example, an appropriate silyl protecting group such as triethylsilane, trimethyl silane or tert-butyldimethylsilyl chloride, in a polar aprotic solvent, for example, THF, in the presence of an excess molar equivalent amount of base, for example, triethylamine, was prepared. The reaction mixture was stirred for about 10 to 20 hours, for example, for about 20 hours. The formation of the bis-protected by-product was quenched by treatment with an aqueous acid/salt solution, for example, sodium chloride in concentrated HCl and water solution, over a period of time from about 30 minutes to 1 hour, for example, for about 50 minutes to a pH of less than 1. These conditions converted any bis-protected by-product to the desired mono-protected product. The solvent was removed by vacuum distillation and then isopropanol was added for crystallization promoted by the addition of seed crystals of the compound of formula (F) at a temperature of between about 5° C. and 15° C., for example, at about 10° C., for a period of time from about 1 hour to 3 hours, for example, for about 2 hours. Water, for example, deionized water, was added to the resulting slurry and the resulting slurry stirred for a period of time from about 10 hours to about 25 hours, for example, for about 20.5 hours. The compound of formula (F) was isolated by filtration, followed by a wash of the solids with an isopropanol/water solution and drying.

Alternatively, to a mixture of the compound of formula (E) and an excess molar equivalent amount of an oxygen-protecting group provider, for example, tert-butyldimethylsilyl chloride, a polar aprotic solvent, for example, THF, was added. Stirring of the resulting mixture commenced at a temperature of between about 20° C. and about 30° C., for example, at room temperature, and a solution was formed after a period of time from about 10 minutes to 30 minutes, for example, at about 11 minutes. An excess molar equivalent amount of base, for example, triethylamine, was added to the reaction mixture over a period of time of between 10 minutes and 30 minutes, for example, over about 13 minutes, as the temperature of the reaction mixture increased to a temperature of between 25° C. and 35° C., for example, to about 30° C. The reaction mixture was stirred for a period of time of between 6 hours to about 48 hours, for example, for about 22.5 hours at room temperature, for example, at 22° C. The reaction mixture was then cooled to a temperature of between about 10° C. and 20° C., for example, to about 13° C. A solution of concentrated acid, for example, HCl, and sodium chloride in DI water was added to the reaction mixture over a period of time from 10 minutes to 1 hour, for example, for 25 minutes, with a temperature rise to between 20° C. and 30° C., for example, to about 21° C. The resulting mixture was brought to a pH of less than 2, for example, to pH 0.84. The resulting biphasic solution was stirred for a period of time of between about 30 minutes to 1 hour, for example, for about 43 minutes, and the stirring was stopped. After a period of time of between 1 hour to 3 hours, for example, for about 2 hours, the mixture was buffered by addition of a solution of sodium acetate in water, for example, in DI water, was added to the reaction mixture. The resulting solution was stirred for a period of time of between about 5 minutes and 20 minutes, for example, for about 5 minutes, and the layers were separated. The organic layer was then distilled under vacuum keeping temperature of between about 20° C. and 35° C., for example, at a temperature of between 22° C. and 30° C., to remove the solvent. Isopropanol was again added and the resulting mixture was distilled again under vacuum at temperature of between about 25° C. and 35° C., for example, at a temperature of between 26° C. and 34° C. to remove the solvent. Isopropanol was added and the resulting mixture stirred for a period of time of between 8 hours and 20 hour, for example, for about 17 hours, at a temperature of between about 20° C. and 25° C., for example, at about 22° C. The mixture was then heated to a temperature of between 40° C. and 60° C., for example, to about 50° C., to give a homogenous solution. Water, for example, DI water, was added to the solution over a period of time from 1 minute to 10 minutes, for example, over about 5 minutes. The reaction mixture was stirred for a period of time from 10 minutes to 20 minutes, for example, for about 15 minutes, and the solution was cooled over a period of time from about 10 minutes to 20 minutes, for example, for about 14 minutes, to a temperature of between about 25° C. and about 35° C., for example, to about 33° C. Seeds of the compound of formula (F) were added to the mixture and the resulting mixture was stirred for a period of time from about 30 minutes to about 2 hours, for example, for about 1 hour, to give crystal growth. Water, for example, DI water, was added to the mixture over a period of time from about 30 minutes to 2 hours, for example, over about 1 hour. Alternatively, seeds of the compound of formula (F) may be added to the mixture before adding the first portion of water. The mixture was then cooled to a temperature of between about 0° C. and 25° C., for example, to about 20° C., and stirred for a period of time of between about 24 hours and 72 hours, for example, for about 68 hours. The compound of formula (F) was isolated by filtration, followed by a wash of the solids with an isopropanol/water solution and drying. The material may be recrystallized if needed using up to 10% isopropanol in heptane solvent mixture.

The compound of formula (F) so formed was then subjected to catalyzed C—C bond formation conditions to provide the compound of formula (G). In particular, to a mixture of the compound of formula (F), less than equimolar amount of a catalyst, for example, a thiourea-substituted hydroquinine derivative, and an equivalent amount of paraformaldehyde was added a non-polar solvent, such as n-heptane. The resulting reaction mixture was stirred at ambient temperature, for example, at about 25° C., for a period of time from about 10 minutes to about 1 hour, for example, for about an hour. An excess molar equivalent amount of an aqueous formaldehyde solution was added to the reaction mixture and the reaction mixture was stirred at ambient temperature, for example, at about 25° C., for a period of time from about 24 hours to 50 hours, for example, for about 47 hours. The crude product was isolated by filtration, non-polar solvent wash, for example, with n-heptane, and drying. The compound of formula (G) was isolated from the crude product by enrichment recrystallization using methanol/acetic acid to form a methanol/acetic acid slurry, followed by filtration of the racemate (Ga) as a filtered solid. Then, the product (compound of formula (G)) precipitated from the filtrate by adding water as anti-solvent, filtration, methanol/water wash and drying.

Optionally, the racemate of the compound of formula (G), i.e., the compound of formula (Ga):

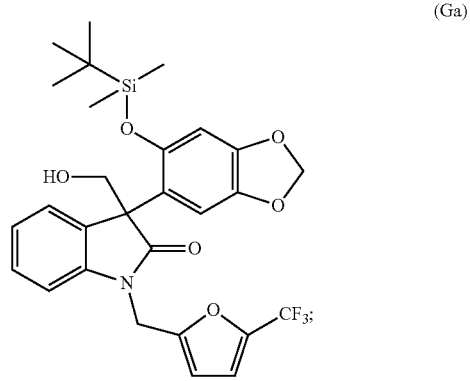 [SMILES: CC(C)(C)[Si](C)(C)Oc1cc2c(cc1C1(CO)C(=O)N(Cc3ccc(C(F)(F)F)o3)c3ccccc31)OCO2]

(Ga)

was isolated from the methanol/acetic acid slurry by filtration (the compound of formula (Ga) was in the filtered solids). The compound of formula (Ga) was then treated under suitable retro-aldol reaction conditions to yield the compound of formula (F), which can then subjected to the catalyzed C—C bond formation conditions above for the compound of formula (F) to provide the compound of formula (G). In general, the racemate of the compound of formula (G), i.e., the compound of formula (Ga), and an excess molar equivalent amount of a formaldehyde scavenger (for example: 2-imidazolidone) were dissolved in a solvent such as isopropanol followed with the addition of a base (for example, triethylamine). The obtained mixture was warmed to about 75° C. to about 100° C. and full dissolution observed. After about 75-120 minutes, the reaction was completed. The mixture was cooled to about 25° C. and water was added slowly (over about 1.5 hours). The resulting slurry was cooled to about −5° C. and mixed for additional 2 to 13 hours. The solid obtained was collected by filtration, washed with mixture of isopropanol and water followed by a water wash. The resulting white solid was dried to afford the compound of formula (F).

Alternatively, to a mixture of a compound of formula (F), a less than equimolar amount of a catalyst, for example, a thiourea-substituted quinine derivative, and an equimolar amount of paraformaldehyde, was added a non-polar solvent, such as n-heptane, under vacuum. The resulting suspension was stirred at a temperature of between about 20° C. and 30° C., for example, at about 26° C., for a period of time from about 10 minutes to 1 hour, for example, for about 20 minutes. An excess molar equivalent amount of aqueous formaldehyde was added to the reaction mixture and the resulting reaction mixture was stirred at a temperature of between about 20° C. and 30° C., for example, at about 26° C., for a period of time from about 30 hours to about 50 hours, for example, for about 47 hours. The crude product was isolated at a temperature of from about 20° C. and 30° C., for example, at about 26° C., and washed with a non-polar solvent, such as n-heptane. The solids were dried under vacuum at a temperature of between about 20° C. and 50° C., for example, at 45° C., for a period of time of between about 30 hours and about 50 hours, for example, for about 40 hours, to give a crude product. The crude product was then suspended in a premixed solution of alkanol and acid, for example, a premixed solution of methanol and acetic acid. The resulting slurry was cooled to a temperature of between about 15° C. and 25° C., for example, to about 20° C. and stirred for a period of time of between about 2 hours and 6 hours, for example, for about 4.5 hours. The combined filtrates were combined and held overnight at room temperature. Water, for example, DI water, was added to the filtrate over a period of time from about 10 minutes to 30 minutes, for example, over 20 minutes, to give crystal growth. Additional water, for example, DI water, was added over a period of time from about 10 minutes to 30 minutes, for example, over 20 minutes. The resulting mixture was stirred for a period of time from about 1 hour to about 3 hours, for example, for about 2 hours, and the solids were isolated at room temperature by filtration. The solids were washed with a premixed solution of alkanol and water, for example, methanol and DI water, and the solids dried on a filter under vacuum to give the compound of formula (G).

The compound of formula (G) so formed was then subjected to deprotection and intramolecular cyclization conditions to form funapide. In particular, to the compound of formula (G) was added a less-than-equivalent molar amount of an aqueous acid solution, for example, aqueous hydrobromic acid, and a polar aprotic solvent, for example, acetonitrile. The resulting reaction mixture containing the deprotected compound of formula (G), i.e., a compound of formula (G'):

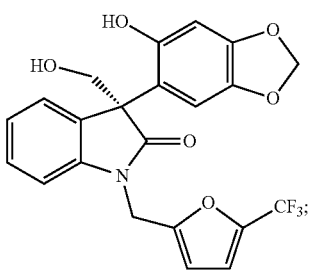
(G')

was heated to a temperature of between 30° C. and 40° C., for example, to about 37° C.±3° C., over a period of time from about 10 minutes to 30 minutes, for example, for about 20 minutes. The reaction mixture was then stirred for a period of time from about 5 hours to about 8 hours, for example, for about 6 hours. The reaction mixture was then cooled to a temperature of between 15° C. and 25° C., for example, to 20° C.±3° C. Optionally, the reaction mixture was extracted with a non-polar, aprotic solvent such as cyclohexane to remove siloxane. An excess molar equivalent amount of a suitable phosphine, for example, chlorodiphenylphosphine, was added to the reaction mixture and the resulting reaction mixture was heated to a temperature of between about 30° C. and about 40° C., for example, to about 37° C.±3° C. The reaction mixture was stirred at this temperature for a period of time from about 8 hours to 24 hours, for example, for about 18 to about 21 hours. The reaction mixture was cooled to a temperature of between about 10° C. and about 30° C., for example, to about 20° C.±5° C. An aqueous solution of hydrogen peroxide in a polar aprotic solvent, for example, acetonitrile, was added to the reaction mixture to convert diphenylphosphine, if utilized above, to the corresponding acid or oxide in order to mitigate the odor associated with diphenylphosphine while not allowing the temperature of the reaction mixture to rise above 35° C. The reaction mixture was cooled to a temperature of between about 10° C. to about 30° C., for example, to about 20° C.±5° C. and then filtered. The resulting solution was then subjected to a solvent exchange with an appropriate alcohol, for example, methanol or ethanol. The resulting reaction mixture was heated to a temperature of between about 55° C. and about 75° C., for example, to about 65° C.±5° C. The reaction mixture was then cooled to a temperature of between about 30° C. and 40° C., for example, to about 35° C.±3° C. and seed crystals of funapide were added. The resulting reaction mixture was stirred for a period of more than 30 minutes, for example, for about 1.5 hours, and additional water was added while maintaining the temperature at about 35° C.±3° C. The reaction mixture was cooled to a temperature of between about 15° C. and about 25° C., for example, to about 22° C.±3° C., over a period of time from about 15 minutes to an hour, for example, for about 30 minutes and maintained at that temperature for a period of time from about 8 hours to about 20 hours, for example, from about 12.5 hours to about 15 hours. Funapide was isolated from the reaction mixture by filtration. The resulting solids were washed with an aqueous solution of an appropriate alcohol, for example, methanol, and DI water, and dried under vacuum. The funapide so formed by the above process was suitable for use in the pharmaceutical compositions of the invention.

Funapide so formed was then optionally treated to a further purification process to remove trace amounts of impurities, such as the compound of formula (E), and other undesired side-products. In particular, to funapide was added basic alumina and an appropriate alcohol, for example, methanol. The resulting mixture was heated to a temperature of between about 55° C. and about 70° C., for example, to about 65° C.±3° C. The reaction mixture was stirred at this temperature for at least 2 hours at which point the reaction mixture may be tested to determine remaining quantity of compound of formula (E). If needed, additional basic alumina was added and the reaction mixture stirred for an additional 2 hours. The alumina was filtered from the reaction mixture and the filtered solution was washed (methanol) for a period of time of between about 10 minutes to about 60 minutes, for example, for about 30 minutes. The resulting reaction mixture was heated to a temperature of between about 55° C. and about 70° C., for example, to about 65° C.±3° C., and then cooled to a temperature of between about 30° C. and about 40° C., for example, to about 35° C.±3° C. over a period of time from between 10 minutes and an hour, for example, over about 30 minutes. Seed crystals of funapide were added to the reaction mixture and the temperature of the reaction mixture was held at a temperature of between about 30° C. and about 40° C., for example, at about 35° C.±3° C., for a period of time of more than 30 minutes, for example, over about 1.5 h. Water, for example, deionized water, was added to the reaction mixture over a period of time of between about 30 minutes and about 1.5 hours, for example, for about an hour, while the temperature was maintained at between about 30° C. and about 40° C., for example, at about 35° C.±3° C. The reaction mixture was cooled to a temperature of between about 15° C. and about 30° C., for example, at about 22° C.±3° C., over a period of time from about 10 minutes to an hour, for example, over about 30 minutes. After a period of time of more than 1 hour, for example, after about 1.5 hours, funapide was isolated from the reaction mixture by filtration, followed by a methanol/water wash and drying under vacuum.

Funapide prepared by the above process demonstrated a greater than 99% purity with respect to any undesired product and greater than 94% chiral (enantiomeric) purity.

A more specific method of preparing funapide by Reaction Scheme 1 above is illustrated below in Reaction Scheme 1A wherein LG$^1$ in the compound of formula (B) above in Reaction Scheme 1 is shown as bromo and PG$^1$ in the compounds of formulae (F) and (G) above in Reaction Scheme 1 is shown below as tert-butyldimethylsilyl:

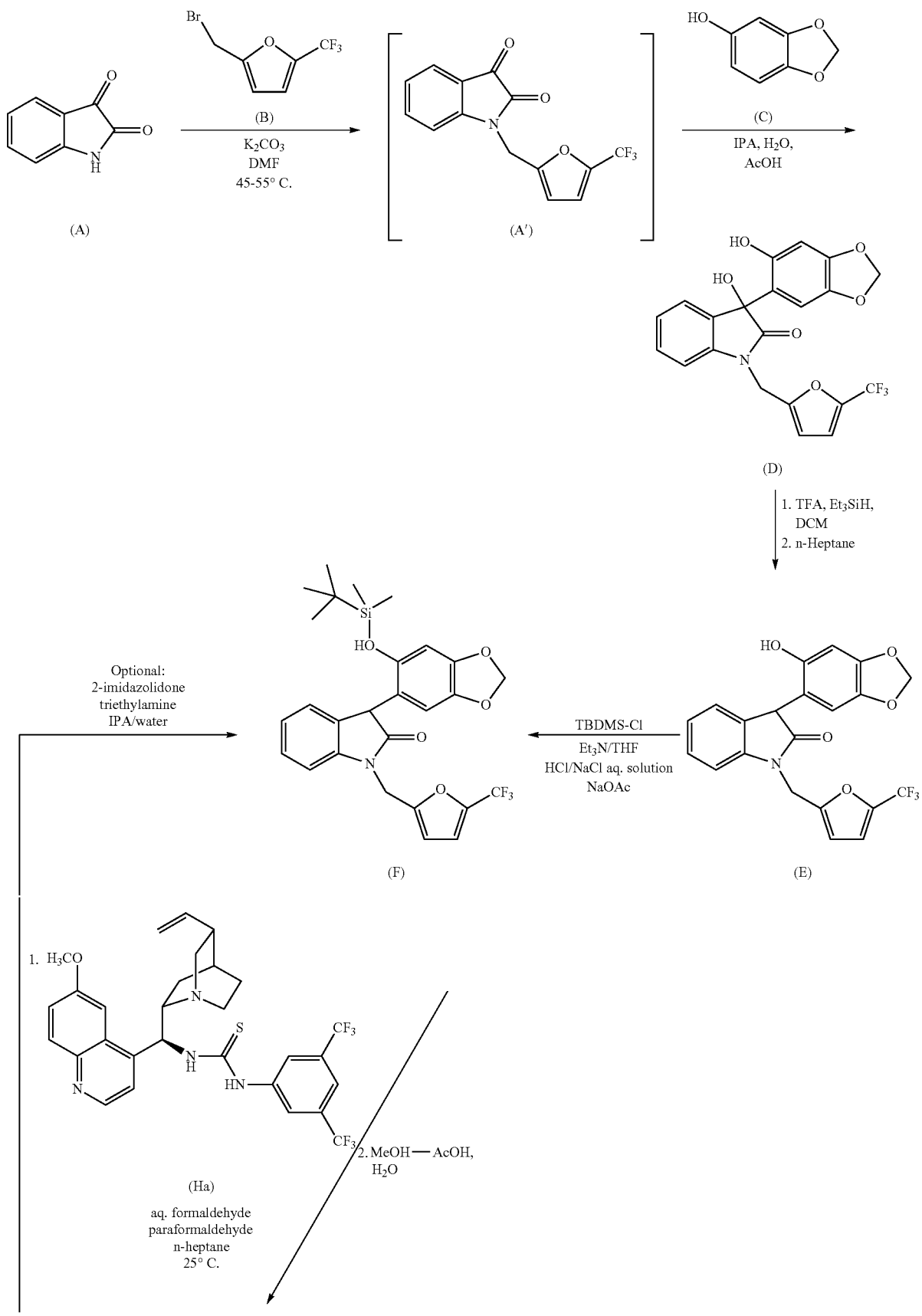
REACTION SCHEME 1A

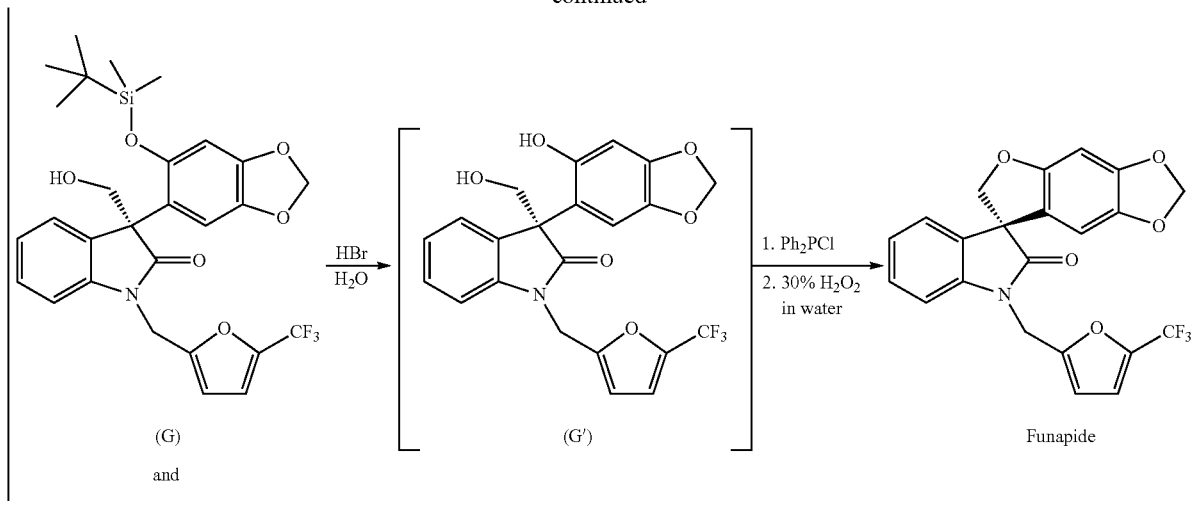

(G)
and (G′)

Funapide

(Ga)

The specific experimental conditions and parameters for the above Reaction Scheme 1A are described in more detail below in the Examples.

An alternative method of preparing the compound of formula (D) utilized above in Reaction Scheme 1 and Reaction Scheme 1A is described below in Reaction Scheme 2 where $LG^1$ is a leaving group such as bromo, chloro, iodo, mesylate or tosylate.

REACTION SCHEME 2

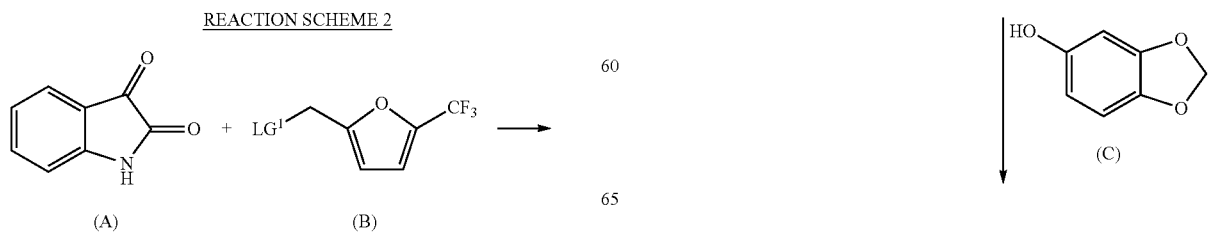

(A)      (B)

-continued

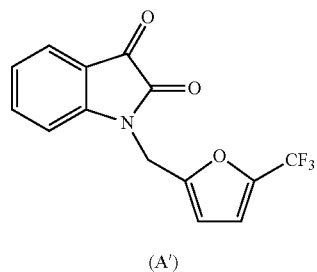

(A′)

(C)

35
-continued

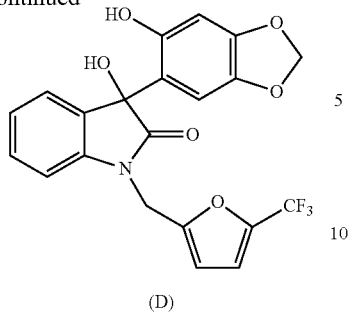

(D)

36
-continued

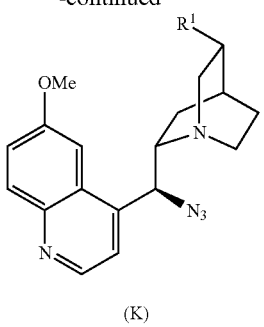

(K)

Ph₃P, H₂O
CH₂Cl₂

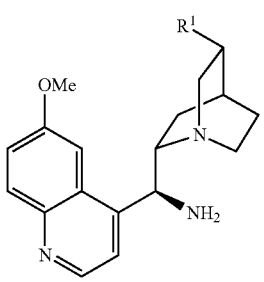

(L)

CH₂Cl₂ or
ethyl acetate

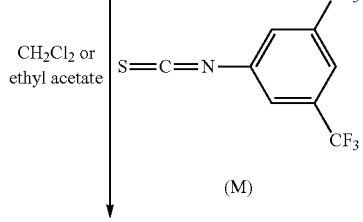

(M)

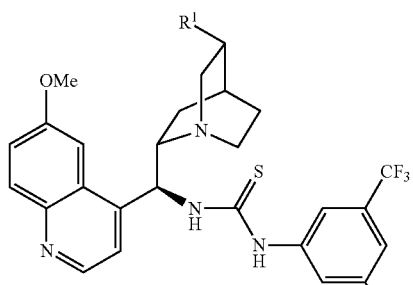

(H)

Compounds of formula (A), (B) and (C) are commercially available or can be prepared according to methods known to one skilled in the art or by the methods disclosed in PCT Published Patent Application No. WO 2006/110917, PCT Published Patent Application No. WO 2010/45251, PCT Published Patent Application No. WO 2010/045197, PCT Published Patent Application No. WO 2011/047174, PCT Published Patent Application No. WO 2011/002708 and PCT Published Patent Application No. WO 2013/154712.

In general, the compound of formula (D) was prepared by the reaction described in Reaction Scheme 1A by first treating the compound of formula (A) in a polar aprotic solvent, such as dimethyl sulfoxide, with a slight excess molar equivalent amount of a compound of formula (B) in the presence of a base, such as cesium carbonate, anhydrous potassium carbonate, sodium hydride, or calcium hydride. The resulting reaction mixture was stirred at ambient temperature for a period of time from about 1 hour to about 24 hours. The compound of formula (A') was isolated from the reaction mixture by standard isolation techniques, such as filtration of undesired products, precipitation and further filtration, followed by a water wash of the solids and drying. The compound of formula (A') so formed can then be dissolved in an appropriate polar aprotic solvent and then treated with sesamol as described above in Reaction Scheme 1 to yield the compound of formula (D), which can then be used in Reaction Scheme 1 as described above to prepare funapide.

Methods for preparing the catalysts utilized in the methods disclosed herein are described below in Reaction Scheme 3 wherein $R^1$ is —CH₂—CH₃ or —CH=CH₂:

REACTION SCHEME 3

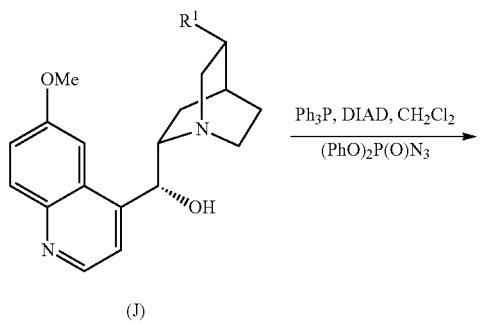

(J)

Ph₃P, DIAD, CH₂Cl₂
(PhO)₂P(O)N₃

Compounds of formula (J) are commercially available. The compound of formula (J) where $R^1$ is —CH₂—CH₃ is hydroquinine and the compound of formula (J) where $R^1$ is —CH=CH₂ is quinine. The compound of formula (H) where $R^1$ is —CH=CH₂ is designated herein as the compound of formula (Ha) and the compound of formula (H) where $R^1$ is —CH₂—CH₃ is designated herein as the compound of formula (Hb) as shown below:

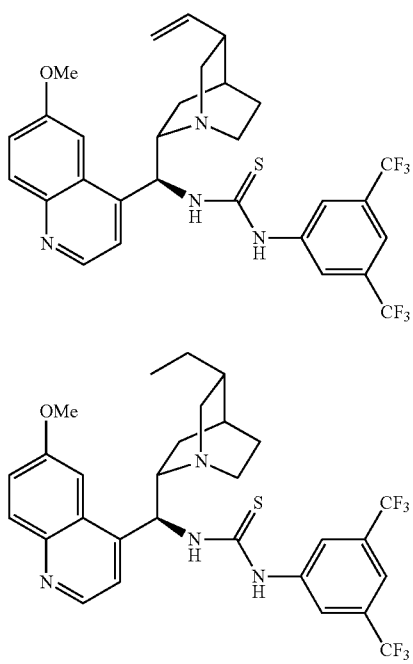

(Ha)

(Hb)

In general, the compound of formula (Ha) is prepared by the process disclosed in Reaction Scheme 3 by first treating a compound of formula (J) where $R^1$ is —CH=$CH_2$ with an excess equivalent amount, such as 1.2 to 1.5 equivalent amount, preferably about 1.2 equivalent amount, of diphenylphosphoryl azide under suitable Mitsunobu reaction conditions, for example, in the presence of an excess equivalent amount, such as 1.2 to 1.5 equivalent amount, preferably about 1.2 equivalent amount, of a phosphine reagent such as, but not limited to, triphenylphosphine, tributylphosphine or trimethylphosphine, and an excess equivalent amount, such as 1.2 to 1.5 equivalent amount, preferably about 1.2 equivalent amount, of an azodicarboxylate of diethyl, diisopropyl or di-tert-butyl in a solvent such as, but not limited to, tetrahydrofuran, toluene, methylene chloride or 2-methyltetrahydrofuran, preferably a non-miscible solvent such as methylene chloride (dichloromethane), at a temperature of between about 0° C. to about 45° C., preferably at about 25° C., for about 1 to 24 hours, preferably for about 2 hours, to afford the compound of formula (K) where $R^1$ is —CH=$CH_2$.

Water is then added to the reaction mixture and the compound of formula (K) where $R^1$ is —CH=$CH_2$ is then reduced under standard reduction conditions, such as treatment with an excess equivalent amount, such as 1.5 to 1.8 equivalent amount, preferably about 1.8 equivalent amount, of a reducing agent, such as triphenylphosphine, in an appropriate solvent, such as, but not limited to, methylene chloride, at a temperature of between about 15° C. to about 28° C., preferably at about 25° C., for about 1 to 24 hours, preferably for about 8 hours. The reaction mixture is acidified with 3N HCl aqueous solution to pH about 1.8 to 3, preferably 2.0 to 2.5. The organic layer is discarded. The aqueous layer is washed with an additional solvent, and basified with aqueous ammonia to pH about 9.5 to 11, preferably 10 to 10.5. The mixture is extracted with an approximate solvent, such as, but not limited to, ethyl acetate, with an amount, about 8 to 10 volumes, preferably 8 volumes to afford a solution of the compound of formula (L) where $R^1$ is —$CH_1$=$CH_2$.

The solution of the compound of formula (L) where $R^1$ is —CH=$CH_2$ is then treated with an amount, such as 0.8 to 1.1 equivalent amount, preferably about 0.9 equivalent amount, of the compound of formula (M) under suitable coupling conditions, such as in a suitable coupling solvent, such as methylene chloride or ethyl acetate, preferably ethyl acetate, for about 0.5 to 20 hours, preferably for about 1 hour, to obtain an complete reaction. The compound of formula (Ha) is isolated from the mixture under suitable conditions, such as acidifying the reaction mixture with 1N HCl to pH about 2.0-3.0, preferably 2.0-2.5. The aqueous layer is then discarded. The organic layer is then basified with aqueous ammonia to pH about 9 to 11, preferably 10 to 10.5, and washed with additional water. The mixture is swapped in an appropriate solvent, such as, but not limited to acetonitrile in an amount of about 1.2 to 1.8 volumes, preferably 1.5 volumes, for recrystallization to afford the compound of formula (Ha).

In general, the compound of formula (Hb) is prepared by the process disclosed in Reaction Scheme 3 by first treating a compound of formula (J) where $R^1$ is —$CH_2$—$CH_3$ with an excess equivalent amount, such as 1.2 to 1.8 equivalent amount, preferably about 1.2 equivalent amount, of diphenylphosphoryl azide under Mitsunobu reaction conditions, for example, in the presence of an excess equivalent amount, such as 1.2 to 1.8 equivalent amount, preferably about 1.2 equivalent amount, of a phosphine reagent such as, but not limited to, triphenylphosphine, tributylphosphine or trimethyl phosphine, and an excess equivalent amount, such as 1.2 to 1.8 equivalent amount, preferably about 1.2 equivalent amount, of an azodicarboxylate of diethyl, diisopropyl or di-tert-butyl in a solvent such as, but not limited to, tetrahydrofuran, toluene, methylene chloride or 2-methyltetrahydrofuran, preferably a non-miscible solvent such as methylene chloride (dichloromethane), at a temperature of between about 0° C. to about 45° C., preferably at about 25° C., for about 1 to 24 hours, preferably for about 2 hours, to afford the compound of formula (K) where $R^1$ is —$CH_2$—$CH_3$.

Water is then added to the reaction mixture and the compound of formula (K) where $R^1$ is —$CH_2$—$CH_3$ is then reduced under standard reduction conditions, such as treatment with an excess equivalent amount, such as 1.2 to 2.0 equivalent amount, preferably about 1.8 equivalent amount, of a reducing agent, such as triphenylphosphine, in an appropriate solvent, such as, but not limited to, methylene chloride, at a temperature of between about 15° C. to about 28° C., preferably at about 25° C., for about 1 to 24 hours, preferably for about 8 to 20 hours. The reaction mixture is acidified with 3N HCl aqueous solution to pH about 1.8 to 3, preferably 2.0 to 2.5. The organic layer is discarded. The aqueous layer is washed with an additional solvent, and basified with aqueous ammonia to pH about 9.5 to 11, preferably 10 to 10.5. The mixture is extracted with an approximate solvent, such as, but not limited to, ethyl acetate, with an amount, about 8 to 10 volumes, preferably 8 volumes, to afford a solution of the compound of formula (L) where $R^1$ is —$CH_2$—$CH_3$.

The solution of the compound of formula (L) where $R^1$ is —$CH_2$—$CH_3$ is then treated with an amount, such as 0.8 to 1.1 equivalent amount, preferably about 0.9 equivalent amount, of the compound of formula (M) under suitable coupling conditions, such as in a suitable coupling solvent, such as tetrahydrofuran, 2-methyltetrahydrofuran or methylene chloride, preferably methylene chloride, for about 0.5 to 20 hours, preferably for about 1 hour, to obtain an complete reaction. The compound of formula (Hb) is isolated from the mixture under suitable conditions, such as acidifying the mixture with 1N HCl to pH about 2.0-3.0, preferably 2.0-2.5. The aqueous layer is then discarded. The organic layer is then basified with aqueous ammonia to pH about 9 to 11, preferably 10 to 10.5, and washed with additional water. The mixture is swapped in an appropriate solvent, such as, but not limited to acetonitrile in an amount of about 1.5 to 2.0 volumes, preferably 1.8 volumes, for recrystallization to afford the compound of formula (Hb).

The specific experimental conditions and parameters for the above Reaction Scheme 3 are described in more detail below in the Examples.

All of the procedures described above and below were performed under standard laboratory conditions, such as under a nitrogen atmosphere.

The following Examples, which are directed to the preparation of the intermediates, starting materials, catalysts and/or funapide are provided as a guide to assist in the practice of the invention, and are not intended as a limitation on the scope of the invention.

Example 1

Synthesis of 3-hydroxy-3-(6-hydroxy-1,3-benzodioxol-5-yl)-1-[[5-(trifluoromethyl)-2-furyl]methyl]indoline-2-one, Compound of Formula (D)

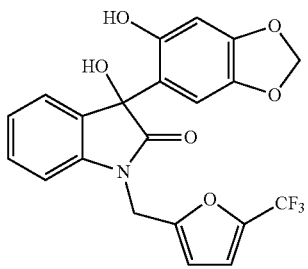 [SMILES: O=C1N(Cc2ccc(C(F)(F)F)o2)c2ccccc2C1(O)c1cc2c(cc1O)OCO2]

A. Solid isatin (compound of formula (A), 9.50 kg, 64.6 mol) was charged via pre-weighed bags to an inerted 50-gal Hastelloy fixed reactor, followed by anhydrous powdered potassium carbonate (22.3 kg, 161 mol, 2.50 equiv, 325 mesh). N,N-dimethylformamide (DMF) (34.2 kg, 3.80 vol) was added and the reactor inerted a second time. The slurry was agitated for 16 minutes to suspend the solids prior to heating to 48±3° C. Neat 2-(bromomethyl)-5-(trifluoromethyl)furan (a compound of formula (B), 14.9 kg, 65.2 mol, 1.01 equiv.) was charged as a slow stream over 61 minutes, controlling the exothermic reaction between 45 and 54° C. The orange-colored reaction mixture was cooled to 30±5° C., and then sesamol (compound of formula (C), 10.0 kg, 72.3 mol, 1.12 equiv) in DMF (6.8 kg, 0.75 vol) was added over 80 minutes. The reaction was stirred at 30° C. for 3 hours to complete the coupling, at which point 0.24 A % of the non-isolated intermediate, 1-((5-(trifluoromethyl)furan-2-yl)methyl)indoline-2,3-dione, compound of formula (A') remained. The reaction mixture was cooled to 22±3° C. and partially filtered and then recharged to the reactor and slurried in DMF (15.2 kg, 1.70 vol). The reaction mixtures was filtered to remove the remaining product, i.e., 3-hydroxy-3-(6-hydroxy-1,3-benzodioxol-5-yl)-1-[[5-(trifluoromethyl)-2-furyl]methyl]indoline-2-one, compound of formula (D), capturing 99.2% of the theoretical amount.

B. The dark filtrate was held overnight at 21° C. in drums, then transferred to a 100-gal glass lined reactor and heated to 50±3° C. Isopropanol (50.7 kg) was charged followed by deionized water (171 kg) at 50±3° C. to form a clear solution. A slurry of seed crystals of the desired product, compound of formula (D), was added. The remaining deionized water (57.0 kg) containing acetic acid (1.43 kg) was added over 1.5 hours. The reaction mixture was stirred for 0.5 hour at 50±3° C. prior to cooling to 20±5° C. over 1 hour. The solid was isolated by filtration at 22° C. The reactor and solids were washed with deionized water (85.5 kg). The solids were dried under vacuum at 60° C. over 24 hours to give 21.3 kg (76%) of the desired product, 3-hydroxy-3-(6-hydroxy-1,3-benzodioxol-5-yl)-1-[[5-(trifluoromethyl)-2-furyl]methyl]indoline-2-one, compound of formula (D), as a light tan solid. Assay: 100 A % (HPLC-UV at 230 nm), KF: 0.43%.

C. Alternatively, a 200 L reactor was inerted, then charged with isatin (compound of formula (A), 9 kg, 61.2 mol, 1.0 equiv), powdered anhydrous potassium carbonate (13.5 kg, 97.7 mol, 1.6 equiv) and DMF (33.6 kg, 4 vol). The resulting slurry was kept under nitrogen and heated to 45° C. over 25 minutes. Neat 2-(bromomethyl)-5-(trifluoromethyl)furan (a compound of formula (B), 14.45 kg, 63.1 mol, 1.03 equiv) was added over 67 minutes such that the internal temperature was kept between 45 and 54° C. Once the addition was complete, the reaction mixture was stirred at 48° C. for 61 minutes to finish the reaction and cooled to 10° C. The reaction mixture was heated to 30° C. and a solution of sesamol (compound of formula (C), 9.3 kg, 67.3 mol, 1.1 equiv) in DMF (8.5 kg, 1 vol) was added over 76 minutes such that the temperature was maintained between 28° C. and 30° C. The reaction mixture was stirred at 30° C. for 3 hours. The internal temperature was lowered to 10° C. The contents of the 200 L reactor were transferred to a 450 L reactor. The 200 L reactor was rinsed with isopropanol (45.4 kg, 6.4 vol) and the rinse solution added to the 450 L reactor. The contents of the 450 L reactor were heated to 53° C. over 23 minutes. Water (212 kg, 23.6 vol) was added over 54 minutes while keeping the reaction temperature between 53 and 55° C. A slurry of the compound of formula (D) seed crystals (0.53 kg, 2 wt. %) in water (1.35 kg) was charged and the mixture agitated for an additional 30 minutes. The contents of the reactor were allowed to cool to 40° C. prior to charging acetic acid (3.6 kg, 59.3 mol, 1 equiv) in water (124 kg, 13.8 vol) over 89 minutes while maintaining the temperature between 41 and 44° C. The reaction solution was cooled to 20° C. over 61 minutes to crystallize a fine, tan-colored solid. The slurry was aged at 20° C. overnight. The solid was collected on a 0.34 m² Aurora filter/dryer, washed with water (81.3 kg, 9 vol) and then dried at 60±5° C. under a reduced pressure for 3 days to afford 3-hydroxy-3-(6-hydroxy-1,3-benzodioxol-5-yl)-1-[[5-(trifluoromethyl)-2-furyl]methyl]indoline-2-one, compound of formula (D) (25.5 kg, 94.1% yield) as a brown solid: purity (HPLC-UV at 230 nm) 98.9% A %; assay (% wt./wt.) 97.0%; identification (IR spectroscopy) conforms to standard.

D. Alternatively, to a slurry of isatin (compound of formula (A), 100 g, 0.68 mol), powdered anhydrous potassium carbonate (282 g, 2.04 mol) and dimethyl sulfoxide (1000 mL, 10 vol) was added neat 2-(bromomethyl)-5-(trifluoromethyl)furan (a compound of formula (B), 187 g, 0.82 mol) dropwise over 20 minutes, keeping the temperature at 25±5° C. The brown-colored slurry stirred at room temperature overnight and then was filtered to remove salts and residual potassium carbonate. The crude product solution was added to water (3000 mL, 30 vol) dropwise to precipitate the product as an orange solid. The slurry was aged for 0.5 hours, and then the product collected by filtration and washed thoroughly with water (500 mL, twice). The wet cake was vacuum dried at 60° C. overnight (applied nitrogen sparge) to give the desired product, i.e., the compound of formula (A'), as shown below:

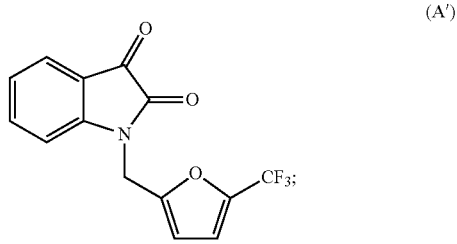 [SMILES: O=C1C(=O)N(Cc2ccc(C(F)(F)F)o2)c2ccccc21]

as an orange solid (193.4 g, 96.4% yield). Purity analysis by HPLC was 100 A %, and $^1$H NMR was consistent with structure. The compound of formula (A') can then be treated with sesamol (compound of formula (C)) to form the compound of formula (D) as described above in Paragraphs A-C.

E. Alternatively, a 1 L reactor was charged with isatin (compound of formula (A), 35 g, 0.24 mol, 1.0 equiv), powdered anhydrous potassium carbonate (52.6 gr, 0.38 mol, 1.6 equiv) and DMF (140 mL, 4 vol). The resulting slurry heated to 45° C. Neat 2-(bromomethyl)-5-(trifluoromethyl)furan (a compound of formula (B), 55.6 g, 0.24 mol, 1.03 equiv) was added over about 1 hour such that the internal temperature was kept between 45 and 55° C. Once the addition was complete, the reaction mixture was stirred at about 45° C. for 30 minutes to finish the reaction. IPC testing result was 0.2% isatin residue. The reaction mixture was heated to 30° C. and a solution of sesamol (compound of formula (C), 36.14 g, 0.26 mol, 1.1 equiv) in DMF (35 mL, 1 vol) was added keeping reaction temperature between 27° C. and 33° C. The reaction mixture was stirred at 30° C. for 4 hours. Then, the reaction mixture was stirred overnight at 5° C. Reaction was completed with IPC result of 0.7% intermediate residue. Water (455 mL, 13 vol.) was added to the reaction mixture at about 20-25° C. following by slow addition (CO$_2$ foaming) of acetic acid (35 mL, 1 vol.). pH 7 was measured at the end of acetic acid addition. Reaction mixture was further stirred during 40 minutes. Then, ethyl acetate (560 mL, 16 vol.) was added to the reaction mixture and after short stirring, phases were separated. The aqueous layer was washed twice with ethyl acetate (88 mL, 2.5 vol.). The organic layers were united and washed three times with water (420 mL, 12 vol.). Ethyl acetate (56 mL, 1.6 vol.) was added to the organic layer and finally washed with water (420 mL, 12 vol.). Ethyl acetate was distilled out until reaction mixture volume reached 3.2 vol (112 mL) and then 105 mL ethyl acetate were added to the mixture. The content of the 1 L reactor was heated to 50-55° C. Heptane (665 mL, 19 vol) was added to the reaction mixture keeping the temperature between 50 and 55° C. Then, the reaction mixture was stirred at 10° C. during about 4 hours. The solid was collected by filtration, washed twice with heptane (2×140 mL, 2×4 vol) and then dried at 45° C. under a reduced pressure to afford 3-hydroxy-3-(6-hydroxy-1,3-benzodioxol-5-yl)-1-[[5-(trifluoromethyl)-2-furyl]methyl]indoline-2-one, compound of formula (D) (89.66 g, 87% yield) as a light tan colored solid: purity (HPLC-UV at 220 nm) 100% A %.

Example 2

Synthesis of 3-(6-hydroxy-1,3-benzodioxol-5-yl)-1-[[5-(trifluoromethyl)-2-furyl]methyl]indoline-2-one, Compound of Formula (E)

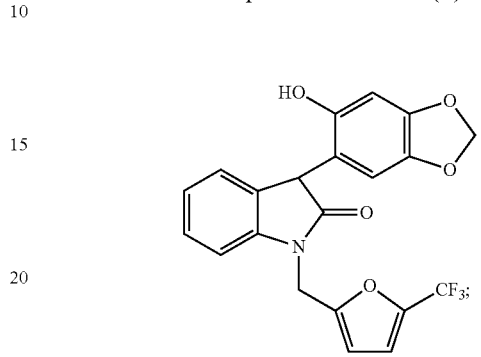

A. Solid 3-hydroxy-3-(6-hydroxy-1,3-benzodioxol-5-yl)-1-[[5-(trifluoromethyl)-2-furyl]methyl]indoline-2-one (compound of formula (D), 18.7 kg, 43.1 mol) was charged to a 100-gal reactor. Methylene chloride (253 kg, 10.0 vol) was added and the resultant slurry was cooled to 0±3° C. over 16 minutes. Triethylsilane (6.64 kg, 1.30 equiv) was added over 2 minutes, keeping the internal temperature at 0±3° C. Trifluoroacetic acid (30.0 kg, 259 mol, 6.0 equiv) was charged to the slurry over 1.0 hour, maintaining the reaction temperature at 10° C. The internal temperature was raised to 25±3° C. for 1 hour to complete the reaction. Deionized water (190 kg, 10 vol) was charged to the reactor. The mixture was stirred at 25° C. for 5 minutes. The stirring was stopped and the contents of the reactor held at 25° C. for 16 minutes, allowing the phases to separate. The lower organic layer was collected in drums and the upper aqueous layer was removed and discarded. The organic layer was returned to the reactor, and then the deionized water washing was repeated two more times. The final wash was with a 10% brine solution (209 kg, 11 vol). Volatile components of the mixture were removed by distillation over a period of 4.3 hours such that 150 L of distillate were collected. The final volume was 35 L in the reactor. Heptane (104 kg, 8 vol) was added and the suspension was stirred for 10 minutes. After cooling to 0° C., the solid was collected by filtration. The off-white crystalline product was washed with heptane (44 kg) and dried at 50-55° C. Yield was 16.4 kg (91.1%) of 3-(6-hydroxy-1,3-benzodioxol-5-yl)-1-[[5-(trifluoromethyl)-2-furyl]methyl]indoline-2-one, compound of formula (E), chemical purity of 100 A % (HPLC-UV, 230 nm).

B. Alternatively, a 450 L reactor was charged with 3-hydroxy-3-(6-hydroxy-1,3-benzodioxol-5-yl)-1-[[5-(trifluoromethyl)-2-furyl]methyl]indoline-2-one (compound of formula (D), 22.0 kg, 50.8 mol, 1.0 equiv), evacuated and filled with nitrogen. Methylene chloride (291 kg, 10 vol) was added and the slurry cooled to 0° C. prior to adding triethylsilane (7.7 kg, 66.2 mol, 1.3 equiv). Trifluoroacetic acid (34.7 kg, 304.2 mol, 6 equiv) was added over 65 minutes while maintaining the temperature from −2 to 0° C. The reaction mixture was warmed to 25° C., and agitated for 90 minutes to complete the reaction. The reaction mixture was washed with water (198 kg, 9 vol), the stirring was stopped and the phases allowed to separate over 30 minutes. The bottom organic phase (product layer) was removed and the upper aqueous layer discarded. The product layer was returned and washed twice more with water (198 kg, 9 vol). The product layer was returned once more and washed with brine (217.8 kg). Volatile components of the mixture were removed by distillation over a period of 5½ hours such that 186 L of distillate was collected. During the course of the distillation n-heptane was added in approximately 10 kg increments per every 15 L distillate removed. The methylene chloride remaining in the reaction mixture was at the 12 wt. % level as determined by quantitative GC. The product slurry was warmed to 30° C. and stirred for 30 minutes followed by cooling to 0° C. The solid was collected on an Aurora filter, washed with n-heptane (56.5 kg, 4 vol) and dried under a reduced pressure at 50° C. to afford 3-(6-hydroxy-1,3-benzodioxol-5-yl)-1-[[5-(trifluoromethyl)-2-furyl]methyl]indoline-2-one, compound of formula (E), 18.7 kg, 88.2% yield) as a yellow solid: purity (HPLC-UV at 230 nm) 98.9 A %.

C. Alternatively, a 1 L reactor was charged with 3-hydroxy-3-(6-hydroxy-1,3-benzodioxol-5-yl)-1-[[5-(trifluoromethyl)-2-furyl]methyl]indoline-2-one (compound of formula (D), 45.0 g, 0.10 mol, 1.0 equiv) and methylene chloride (450 mL, 10 vol). Then, the slurry cooled to below than 0° C. prior to adding triethylsilane (15.7 g, 0.13 mol, 1.3 equiv). Trifluoroacetic acid (71.0 g, 0.62 mol, 6 equiv) was added over 17 minutes while temperature raised up to 11° C. The reaction mixture was warmed to 25° C., and agitated for 60 minutes to complete the reaction. The reaction mixture was washed with water (450 mL, 10 vol), the stirring was stopped and the phases allowed to separate. The bottom organic phase (product layer) was removed and the upper aqueous layer discarded. The product layer was returned and washed twice with water (450 mL, 10 vol.). The product layer was returned once more and washed with brine (450 mL). Volatile components of the mixture were removed until 6 volumes (270 mL) of reaction mixture left. 180 mL (4 vol.) n-heptane were added twice and distilled until 6 volumes of reaction mixture remained each time. Then isopropanol (90 mL, 2 vol.) was added to the reaction mixture and the slurry was further stirred at about −5° C. overnight. The solid was collected by filtration, washed with n-heptane (2×90 ml, 2×2 vol.) and dried under a reduced pressure at 50° C. to afford 3-(6-hydroxy-1,3-benzodioxol-5-yl)-1-[[5-(trifluoromethyl)-2-furyl]methyl]indoline-2-one, compound of formula (E), 43.6 g, 87% yield) as a yellow solid: purity (HPLC-UV at 220 nm) 100.0 A %.

Example 3

Synthesis of 3-(6-tert-butyldimethylsilyloxy-1,3-benzodioxol-5-yl)-1-[[5-(trifluoromethyl)-2-furyl]methyl]indoline-2-one, a Compound of Formula (F)

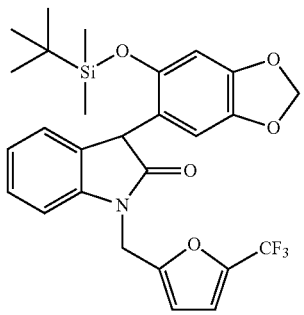 [SMILES: CC(C)(C)[Si](C)(C)Oc1cc2c(cc1C1C(=O)N(Cc3ccc(C(F)(F)F)o3)c3ccccc31)OCO2]

A. A reactor was charged with 3-(6-hydroxy-1,3-benzodioxol-5-yl)-1-[[5-(trifluoromethyl)-2-furyl]methyl]indoline-2-one (compound of formula (E), 16.2 kg, 38.8 mol) and tert-butyldimethylsilyl chloride (7.60 kg, 50.4 mol, 1.3 equiv). Tetrahydrofuran (57.7 kg, 4 vol) was added and the mixture was placed under nitrogen and stirring started. Once a solution formed, triethylamine (8.63 kg, 85.3 mol, 2.2 equiv) was added over 14 minutes. The reaction was stirred for 20 hours, at which time no compound of formula (E) was detected. A solution of conc. HCl (36.5-38%, 4.01 kg, 1.05 eq) and sodium chloride (8.02 kg) in deionized water (43.3 kg, 2.7 vol) was added over 50 minutes to pH 0.85. The temperature of the reaction mixture was between 11-16° C. during the addition. The reaction mixture was warmed and stirred at 22° C. for 30 minutes. The top layer was sampled and no bis-silylated side-product was detected by HPLC. The reaction mixture was next distilled to remove 32.6 kg (37 L) of solvent over 140 minutes. Isopropanol (12.7 kg, 1.0 vol) was added and the distillation resumed. This removed 12.7 kg (14 L) of solvent over 4.75 hours. Isopropanol (57.2 kg, 4.5 vol) was added and the IPC test showed a 155:1 ratio of isopropanol/tetrahydrofuran. Tetrahydrofuran (5.25 kg) was added and the reaction mixture was cooled to 10° C. Seeds of the desired product, 3-(6-tert-butyldimethylsilyloxy-1,3-benzodioxol-5-yl)-1-[[5-(trifluoromethyl)-2-furyl]methyl]indoline-2-one (a compound of formula (F), 40 g, 0.0019 eq), were added and crystallization was observed after 37 minutes at 10° C. The mixture was stirred for 2 hours. Deionized water (13.0 kg, 0.8 vol) was added over 25 minutes between 11-13° C. After 15 minutes, the remaining deionized water (27.5 kg, 1.7 vol) was added over 28 minutes from 14-16° C. The slurry was stirred for 20.5 hours, then isolated using an Aurora filter. The solids were washed with isopropanol/deionized water (1:1, 48.6 L, 3.0 vol). The solids were dried on the Aurora filter at less than 30° C. for 22 hours. The solids were transferred into the tray dryer and dried for 26 hours at 28-30° C. TGA showed 0.07% weight loss at this point. This gave 18.2 kg (88%) of 3-(6-tert-butyldimethylsilyloxy-1,3-benzodioxol-5-yl)-1-[[5-(trifluoromethyl)-2-furyl]methyl]indoline-2-one, a compound of formula (F), as a white solid with 100 A % purity.

B. Alternatively, a 50-gallon reactor was charged with 3-(6-hydroxy-1,3-benzodioxol-5-yl)-1-[[5-(trifluoromethyl)-2-furyl]methyl]indoline-2-one (compound of formula (E), 18.1 kg, 43.4 mol) and tert-butyldimethylsilyl chloride (8.50 kg, 56.4 mol). The reaction mixture was placed under nitrogen and THF (64.4 kg) was added. Stirring of the reaction mixture was started and a solution formed within 11 minutes at 21° C. Triethylamine was added to the reaction mixture over 13 minutes, giving a temperature increase to 30° C. The reaction mixture was stirred for 22.5 hours at 22° C. and then cooled to 13° C. A solution of conc. HCl (4.53 kg) and sodium chloride (8.95 kg) in DI water (48.9 kg) was added over 25 minutes, giving a temperature increase to 21° C. This addition brought the mixture to pH 0.84. The biphasic solution was stirred for 43 minutes and then the stirring was stopped. After a few hours, a solution of sodium acetate (1.07 kg) in DI water (7.25 kg) was added. The resulting reaction mixture was stirred for 5 minutes and then the layers were separated. The top layer was kept at room temperature for 16 hours. The top layer solution was then distilled with 115-133 mmHg vacuum at an internal temperature of between 22° C. and 30° C. to remove 44.3 kg (50 L) of distillate (solvent). Isopropanol (14.2 kg) was added and the solution was distilled with 62-73 mmHg vacuum and internal temperature of between 26° C. and 34° C. to remove 19.0 kg (22 L) of distillate (solvent). Isopropanol (57.1 kg) was added and the resulting mixture stirred for 17 hours at 22° C. The mixture was then heated to 50° C. to give a homogeneous solution. DI water (7.24 kg) was added to the solution over 5 minutes. After stirring for 15 minutes, the solution was cooled to 33° C. over 14 minutes. Seeds of the compound of formula (F) (0.5 wt %) were added and the mixture stirred for 1 hour, giving crystal growth. DI water (39.8 kg) was added to the mixture over 1 hour. After holding for 30 minutes, the mixture was cooled to 20° C. and then stirred for 68 hours. The solids were isolated from the mixture by filtration. The reactor and the isolated solids were washed with a premixed solution of isopropanol (28.5 kg) and DI water (18.1 kg). The isolated solids were dried under vacuum at temperature of between 35° C. and 39° C. for 89 hours. This gave 21.1 kg (91.7%) of 3-(6-tert-butyldimethylsilyloxy-1,3-benzodioxol-5-yl)-1-[[5-(trifluoromethyl)-2-furyl]methyl]indoline-2-one, a compound of formula (F), as a white solid with 99.8 A % purity.

C. The racemate of the compound of formula (G), i.e., the compound of formula (Ga) (chemical formula $C_{28}H_{30}F_3NO_6Si$, molecular weight 561.63), as prepared below in Example 6, (150 gr), was loaded to 1 L glass reactor followed by addition of 2-imidazolidone (2.5 eq., 57.49 gr), 3 volumes of isopropanol (450 ml) and triethylamine (1 eq., 27.03 gr). The obtained mixture (white slurry) was warmed to 100° C. (in jacket). Full dissolution was not observed when temperature in the reactor reached 78° C. because of the filtering aid present with the compound of formula (Ga) (the filtering aid did not dissolve). After 120 minutes, the reaction was completed (1.03% of the compound of formula (G) was left) and the reactor temperature reached 84° C. The mixture was cooled to 50° C. in jacket when the temperature in reactor reached ~45° C. The reaction mixture was filtered from the filtering aid and the resulting cake was washed with 1 vol. of hot isopropanol (~45° C.). Solution was added back to reactor and cooled to 25° C. in jacket. After the solution reached ~25° C., 3 volumes of water were added slowly (in about 1.5 hours) with dip-pipe. The resulting slurry was cooled according to reactor jacket temperature from 25° C. to −5° C. and mixed for additional ~13 hours. The solid obtained was collected by filtration, washed with mixture of isopropanol and water (150 mL water and 150 mL isopropanol) and then washed with 2 volumes of water. The resulting white solid was dried in vacuum oven at 45° C. over the weekend to obtain a dry solid, the compound of formula (F): Yield: 120.2 gr, 85%; % CP by HPLC: 99.1%.

D. When a filtering aid is not present with the compound of formula (Ga), the procedure in Paragraph C above was performed without having to filtering out the filtering aid by adding 4 volumes of isopropanol instead of 3 volumes. After the reaction was completed, the solution was cooled directly to 25° without having to first cool the solution to 50° C. All other steps remained the same to provide the compound of formula (F).

Example 4

Synthesis of 1-(3,5-bis(trifluoromethyl)phenyl)-3-((1S)-(6-methoxyquinolin-4-yl)((2R)-8-vinylquinuclidin-2-yl)methyl)thiourea, Compound of Formula (Ha)

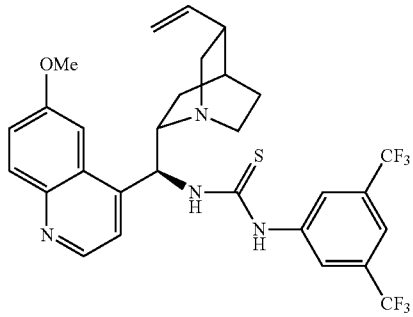

(Ha)

A. A 20 L jacketed reactor, equipped with an overhead stirrer, thermocouple, reflux condenser, and nitrogen sweep, was charged with 1000.3 g (3082.5 mmol, 1.0 eq) of quinine and 970.4 g (3699.7 mmol, 1.2 eq) of triphenylphosphine. The reactor was then charged with 6 L (6 V) of methylene chloride. The reaction mixture was agitated until all solids went into solution. After stirring for 1 hour, the reaction mixture was cooled to 0° C., and 725 mL (3699.7 mmol, 1.2 eq) of diisopropyl azodicarboxylate was added over 1 hour while keeping the temperature at 0±10° C. A solution of 796 mL (3699.7 mmol, 1.2 eq) of diphenylphosphorylazide in 1 L (1 V) of methylene chloride was added to the reactor over 1.5 hours while keeping the reaction mixture temperature at 0±10° C. The reaction mixture was warmed to 25° C., and stirred at this temperature for 1 hour. The reactor was cooled to 15° C. and 1350 mL of DI water was charged. This was followed by the addition of 1454.9 g (5546.9 mmol, 1.8 eq) of triphenylphosphine in 1350 mL (1.5V) of methylene chloride over 1 hour to the reaction mixture while keeping the temperature at 25±5° C. The batch was agitated at 25° C. overnight before cooling back to 20° C. To the reaction mixture was charged 2300 mL of a 3 N HCl solution until the pH of the reaction mixture was 2.0-2.5. After stirring for 20 minutes, the agitator was stopped, and the layers were allowed to separate. The bottom organic layer was drained and set aside. The upper aqueous layer was washed twice with 2600 mL (2.6 V) of methylene chloride, and basified by a charge of approximately 1000 mL of ammonium hydroxide until the pH of the reaction mixture was adjusted to be over 10. The resulting reaction mixture was extracted with 1000 mL (10 V) of ethyl acetate by stirring at room temperature for 15 minutes. The agitation was stopped and the layers allowed to separate. The lower aqueous layer was drained and set aside. The organic layer was washed with additional 2600 mL (2.6 V) of DI water, and distilled under reduced pressure. After approximately half of the solvent was distilled, fresh ethyl acetate was charged. The distillation continued until the water content was less than 700 ppm. A total of 16 L of fresh ethyl acetate was used.

B. The reaction mixture prepared in Paragraph A was cooled to 0° C. A solution of 753.8 g (2779.7 mmol, 0.9 eq.) of 3,5-bis(trifluoromethyl)phenylisocyanate in 2000 mL (2 V) of ethyl acetate was prepared, and charged to the reaction mixture while keeping the reaction mixture temperature at 0±10° C. The reaction mixture was warmed to 20° C. and stirred for approximately 1 hour. The reaction was quenched with 3400 mL of 1 N HCl solution until the pH was adjusted to 2.43. After partition, the upper organic layer was washed with additional 3400 mL (3.4 V) of DI water, and basified with 400 mL of ammonium hydroxide solution until the pH was 10.30. Approximately 3400 mL (3.4 V) of DI water was added and the reaction mixture stirred for additional 15 minutes. The stirring was stopped and the bottom aqueous layer was drained. The remaining ethyl acetate solution was heated to 40° C. after a charge of 3500 mL (3.5 V) of DI water. The batch was stirred for 15 minutes and held at the same temperature overnight without stirring. After complete separation of two layers, the bottom aqueous layer was drained, and vacuum distillation of the organic solution began. After approximately half the solvent was removed, the reaction mixture was cooled to 40° C. before charging additional 4 L of fresh acetonitrile. The distillation continued and the process was repeated until the residual water was below 700 ppm.

C. The vacuum was removed, the reaction mixture prepared in Paragraph B was heated to 80° C. to achieve a clear solution before cooling back to 20° C. in 1 hour. The product precipitated, and the batch was further cooled to 0° C. and stirring for additional 24 hours. The solids were filtered, washed with 575 mL of cold acetonitrile, and dried under a stream of nitrogen to furnish 1093.7 g of 1-(3,5-bis(trifluoromethyl)phenyl)-3-((1S)-(6-methoxyquinolin-4-yl)((2R)-8-vinylquinuclidin-2-yl)methyl)thiourea (compound of formula (IIa)), 59% yield, 97.1 A % purity.

D. Alternatively to the synthesis described above in Paragraphs A-C, a 100 gallon glass-lined jacketed reactor equipped with a −20° C. condenser and thermocouple was inerted with nitrogen. Following a successful vacuum check, the reaction was vented to atmospheric pressure with nitrogen. Quinine (11.00 kg, 33.9 mole, 1.0 eq.) and triphenylphosphine powder (10.70 kg, 40.7 mole, 1.2 eq) were charged to the reactor. This was followed by a charge of methylene chloride (88.15 kg, 6 volumes). The batch was agitated at 25.8° C. for approximately 2 hours to obtain a clear solution. After cooling to 0±5° C., a solution of diisopropyl azodicarboxylate (DIAD, 8.20 kg, 40.7 mole, 1.2 eq.) was charged through an addition tank over approximately 1 hour while maintaining the temperature below 10° C. The addition tank and transfer lines were rinsed with additional methylene chloride (2.70 kg, 1V), and the rinse combined with the batch. This was followed by the charge of a solution of diphenylphosphoryl azide (DPPA, 11.27 kg, 40.7 mole, 1.2 eq.) in methylene chloride (14.77 kg, 1 volume) over approximately 2.5 hours while maintaining the batch temperature below 10° C. Following the addition, the batch was heated to 20±5° C. and agitated for additional 19 hours until the reaction completed.

E. The batch of Paragraph D was cooled to 15±5° C., DI water (14.90 kg, 1.35 V) was charged, followed by a charge of the solution of triphenylphosphine (16.00 kg, 61.0 mole, 1.8 eq.) in methylene chloride (21.70 kg, 1.5 V) over approximately 50 minutes with off-gassing occurring. After addition, the batch was warmed to 25±5° C. and stirred overnight until the reaction completed. Workup started with quenching the batch with 3 N HCl over approximately 1 hour until the pH reached 2.45. The agitation was stopped, and the batch was held at ambient temperature for approximately 1 hour to obtain a clear phase cut. The bottom organic layer was drained into a poly-lined drum. The upper aqueous layer was washed with methylene chloride (2×38.40 kg, 5.2 V). The pH value of the batch was sequentially adjusted with aqueous ammonia (15.75 kg) to 10.02, and the batch was extracted with ethyl acetate (98.70 kg, 10 V), washed with saturated brine (37.2 kg). The resultant solution was heated for vacuum distillation, with continuous charge of the fresh ethyl acetate in portions, until the KF analysis indicated 410 ppm of water in the solution of approximately 8 V of ethyl acetate.

F. The batch of Paragraph E was cooled to 0±5° C. A solution of 3,5-bis(trifluoromethyl)phenyl isothiocyanate (8.30 kg, 30.5 mole, 0.9 eq.) in ethyl acetate (19.75 kg, 2V) was charged into the batch over 30 minutes while maintaining the temperature at 0±5° C. After addition, the batch was warmed to 20±5° C., and stirred for additional 1 hour until reaction completed. The batch was quenched with 1 N HCl (37 L) until the pH reached 2.0-2.5, which was stirred for additional 20 minutes and held until a clear phase cut was reached. The lower aqueous layer was discarded. The organic layer was washed with additional 37.5 kg of DI water (3.4 V), and the pH was adjusted to over 10 with aqueous ammonia. DI water (34.10 kg, 3.1 V) was charged, and the batch was agitated for 10 minutes. The agitation was stopped, and the layers were allowed to separate. The lower aqueous layer was discarded, and the remaining organic solution was heated to 40° C., washed with an additional 34.40 kg of DI water (3.1 V). Agitation was stopped and the batch was held for approximately 5 hours at 40° C., allowing for a clear phase cut. The lower aqueous layer was discarded, the upper organic layer was heated for vacuum distillation, with continuous charge of the fresh acetonitrile (10 V) in portions, until the KF analysis indicated 339 ppm of water remaining in the solution contained 43.3 wt % of the compound of formula (IIa), as determined by a weight assay.

G. The batch of Paragraph F was cooled to 25° C. Solids precipitated when the batch reached 31.5° C., so no seeding was necessary. The batch was cooled to 0° C. over 1 hour, and agitated at 0° C. for additional 16 hours. The slurry was filtered through an Aurora filter, and the filter cake was washed with approximately 8.80 kg of acetonitrile. The product was dried under vacuum at 50° C. for 3 days, affording 14.236 kg of compound of formula (IIa) as a white solid, representing a 70.7% yield. The HPLC weight assay purity was determined as 95.3%, with 3.9 A % of the compound of formula (IIb) as the major impurity. $^1$H NMR (DMSO-$d_6$, 400 MHz): δ=0.77-0.83 (m, 1H), 1.22-1.28 (m, 1H), 1.56-1.63 (m, 3H), 2.28 (brm, 1H), 2.67-2.72 (m, 2H), 3.21 (dd, J=10.0, 13.2 Hz, 1H), 3.24-3.33 (m, 2H), 3.97 (s, 3H), 4.94 (d, J=10.4 Hz, 1H), 5.00 (d, J=17.2 Hz, 1H), 5.83 (ddd, J=7.6, 10.4, 17.2 Hz, 1H), 6.04 (brs, 1H), 7.45 (dd, J=2.8, 9.2 Hz, 1H), 7.62 (d, J=4.8 Hz, 1H), 7.70 (S, 1H), 7.94 (S, 1H), 7.96 (d, J=9.2 Hz, 1H), 8.15 (s, 2H), 8.74 (d, J=4.8 Hz, 1H), 8.96 (d, J=4.8 Hz, 1H), 10.21 (brs, 1H); $^{13}$C NMR (100.59 MHz, DMSO-$d_6$) δ 25.27, 26.92, 27.34, 40.96, 55.05, 55.61, 59.33, 103.02, 114.22, 115.78, 120.62 (brs), 121.24, 123.18 (q, J=272.6 Hz), 127.97, 130.36 (q, J=33.2 Hz), 131.18, 141.68, 141.89, 144.01, 144.91, 147.61, 157.08, 179.43; HRMS-ESI (m/z): [M+H]$^+$ Calculated for $C_{29}H_{29}F_6N_4OS$: 595.1961; found: 595.1975.

Example 5

Synthesis of 1-(3,5-bis(trifluoromethyl)phenyl)-3-((1S)-((2R)-8-ethylquinuclidin-2-yl)(6-methoxyquinolin-4-yl)methyl)thiourea, Compound of Formula (IIb)

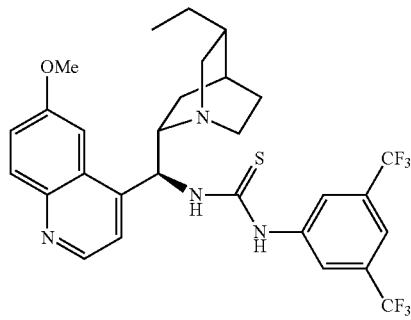

A. To a 20 L jacket reactor, equipped with condenser, thermocouple and nitrogen sweep, was charged 1.2 kg of hydroquinine (3.676 mole, 1.0 eq), 1157.1 g of triphenylphosphine (4.411 mole, 1.2 eq.). The reaction was then charged with 7.2 L (6.0 vol) of methylene chloride. The reaction mixture was stirred at room temperature for approximately 10 minutes to afford a clear solution and then cooled to 0±5° C. Ca. 888.0 g of diisopropyl azodicarboxylate (DIAD, 4.411 mole, 1.2 eq.) was added to the reaction mixture over 45 minutes while keeping the temperature to less than 5° C. After the temperature of the reaction mixture was stabilized at 0-5° C., a solution of 1215.9 g (4.411 mole, 1.2 eq.) of diphenylphosphoryl azide (DPPA) in 1.2 L (1 vol) of methylene chloride was added over an hour to the reaction mixture while keeping the temperature at 0±5° C. The reaction mixture was warmed to 20±5° C. and stirred at this temperature for approximately 2 hours.

B. The reaction mixture prepared in Paragraph A above was cooled to 15±5° C. and 1621.0 g (1.35 vol) of DI water was added, followed by addition of a solution of 1735.6 g (6.617 mole, 1.8 equiv) of triphenylphosphine in 1.8 L (1.5 vol) of methylene chloride over an hour while keeping the temperature at 20±5° C. The reaction mixture was stirred at 23±5° C. for additional 15-18 hours before quenching with approximately 2.8 L of 3N HCl until pH=2.22. After extraction with aqueous acid, the desired product was present in the upper aqueous layer. The aqueous layer was then washed twice with 3.12 L (2.6 vol) of methylene chloride at ambient temperature. The pH of the aqueous layer was adjusted to over 10 by adding 750 mL of ammonium hydroxide (0.625 vol). The resulting mixture was extracted twice with 3.12 L (2.6 vol) of methylene chloride. The desired product was in the bottom organic layer, which were combined and concentrated to dryness, affording 1518 g of crude product as an yellow oil. The residue was further azotropically dried by adding fresh 3 L (2.5 vol) of methylene chloride and continuously concentrating to dryness. The residue again was dissolved in 3 L (2.5 vol) of fresh methylene chloride.

C. To a 20 L jacketed reactor, equipped with condenser, thermocouple and nitrogen sweep, was added the solution of Paragraph B above to 3 L (2.5 vol) of methylene chloride. An additional 3 L (2.5 vol) of methylene chloride was next added to the reaction mixture. The reaction mixture was cooled to 0±5° C. A solution of 897.6 g of 3,5-bis(trifluoromethyl)phenyl isothiocyanate (3.309 mol., 0.9 eq.) in 2.4 L (2 vol) of methylene chloride was added over 35 minutes while keeping the reaction temperature to less than 10° C. The resulting solution was warmed to 20±5° C., and stirred at this temperature for approximately 1 hour, transferred to a rotary evaporator and then concentrated to dryness. The residue was re-dissolved in 9.6 L of ethyl acetate (8 vol), and added back to the 20 L jacket reactor. The pH of the solution was adjusted to approximately 2 by adding 4 L (3.3 vol) of 1N HCl. The reaction mixture was stirred at ambient temperature for 20 minutes and partitioned. The desired product was in the upper organic layer, which was sequentially washed with an additional 4 L (3.3 vol) of DI water. The pH of the organic layer was adjusted to over 10 by adding 950 mL (0.8 vol) of ammonium hydroxide. The reaction mixture was partitioned and the product was in the upper organic layer, which was washed again with 2.4 L (2 vol) of DI water. The ethyl acetate solution was then transferred to a rotary evaporator and concentrated to dryness. The residue was azeotropically dried with 39 L (32.5 vol) of methylene chloride to afford a waxy yellow solid, which was further dried at ambient temperature for an additional 2 days to furnish a first lot of 1990 g of crude product in 95.2 A % purity.

D. A second lot of crude product was prepared with 1.2 kg of hydroquinine using the similar process described above except the ethyl acetate solution was dried with 2.52 kg of anhydrous sodium sulfate before azeotropic drying with methylene chloride. This modification significantly reduced the solvent volume to 8 L (6.7 vol) and the time period needed for the process. The second lot yielded 2129.7 g of the crude product in 95.1 A % purity.

E. To a 20 L jacketed reactor, equipped with condenser, thermocouple and nitrogen sweep, was added 4119.7 g of the combined first and second lots of the crude product. The containers of the two lots were rinsed twice with 2 L (0.49 vol) of acetonitrile. The wash was added to the reactor, along with additional 3.4 L (0.83 vol) of acetonitrile. The mixture was heated to 80° C. to furnish a clear solution. The mixture was then cooled to 28° C. over 3.5 hours, and the desired product began precipitating at approximately 55° C. The mixture was cooled over an hour to 0±5° C. and stirred at this temperature for an additional 17 hours and then filtered. The filter cake was washed twice with 2 L (0.49 vol) of cold acetonitrile and dried for approximately 42 hours to yield 3211.1 g of 1-(3,5-bis(trifluoromethyl)phenyl)-3-((1S)-((2R)-8-ethylquinuclidin-2-yl)(6-methoxyquinolin-4-yl)methyl)thiourea (compound of formula (Hb)), 73.3% overall yield in 98.3 A % purity. $^1$H NMR (DMSO-$d_6$, 400 MHz): δ=0.75-0.82 (m, 4H), 1.15-1.27 (m, 3H), 1.39-1.46 (m, 2H), 1.55 (brs, 1H), 1.60-1.63 (m, 1H), 2.40-2.44 (m, 1H), 2.65-2.73 (m, 1H), 3.18 (dd, J=3.6, 13.2 Hz, 1H), 3.26-3.29 (m, 1H), 3.97 (s, 3H), 6.02 (brs, 1H), 7.45 (dd, J=2.4, 9.2 Hz, 1H), 7.61 (d, J=4.8 Hz, 1H), 7.69 (s, 1H), 7.94 (brs, 1H), 7.96 (d, J=9.2 Hz, 1H), 8.15 (s, 2H), 8.74 (d, J=4.4 Hz, 1H), 8.92 (brs, 1H). 10.22 (brs, 1H); $^{13}$C NMR (100.59 MHz, DMSO-$d_6$) δ 11.79, 24.73, 25.06, 26.73, 28.04, 36.57, 41.01, 55.55, 56.71, 59.27, 102.98, 119.07, 120.54, 123.14 (d, $J_{CF}$=273.6 Hz), 121.21, 127.96, 130.31 (q, $J_{CF}$=33.2 Hz), 131.13, 141.67, 143.96, 145.05, 147.58, 157.01, 179.37; HRMS-ESI (m/z): [M+H]$^+$ Calculated for $C_{29}H_{31}F_6N_4OS$: 597.2117; found: 597.2123.

Example 6

Synthesis of (S)-3-hydroxymethyl-3-(6-tert-butyldimethylsilyloxy-1,3-benzodioxol-5-yl)-1-[[5-(trifluoromethyl)-2-furyl]methyl]indoline-2-one, Compound of Formula (G)

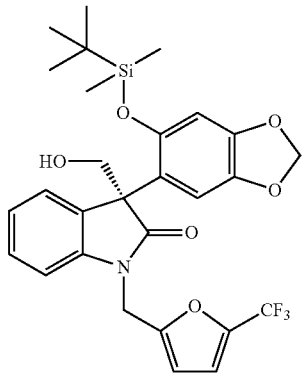 [SMILES: CC(C)(C)[Si](C)(C)Oc1cc2c(cc1[C@@]1(CO)C(=O)N(Cc3ccc(C(F)(F)F)o3)c3ccccc31)OCO2]

A. A glass-lined reactor was charged with 3-(6-tert-butyldimethylsilyloxy-1,3-benzodioxol-5-yl)-1-[[5-(trifluoromethyl)-2-furyl]methyl]indoline-2-one (compound of formula (F), 19.2 kg, 36.1 mol), a catalyst, i.e., the compound of formula (Hb) (238 g, 0.399 mol, 0.0110 equiv), and paraformaldehyde (1.08 kg, 36.1 mol, 1.0 equiv). n-Heptane (144 kg, 11 vol) was added. A nitrogen sweep was established and the suspension stirred at 25° C. for 20 minutes. Aqueous formaldehyde (37% in H$_2$O, 3.23 kg, 39.7 mol, 1.1 equiv) was added in one portion. The reaction was stirred at 25° C. for 47 hours, at which point 3.0 A % of 3-(6-tert-butyldimethyl-silyloxy-1,3-benzodioxol-5-yl)-1-[[5-(trifluoromethyl)-2-furyl]methyl]indoline-2-one, a compound of formula (F), remained. The crude product was isolated at 25° C. by filtration. The initial filtration took 16 minutes. The crude product was washed with n-heptane (99%, 19.8 kg, 1.5 vol). The solids were dried on the Aurora filter under vacuum at 45° C. to give 19.5 kg (96%) of crude (S)-3-hydroxymethyl-3-(6-tert-butyldimethylsilyloxy-1,3-benzodioxol-5-yl)-1-[[5-(trifluoromethyl)-2-furyl]methyl]indoline-2-one, a compound of formula (G). The chiral purity of the solids was 70.5% ee. The crude product was charged back into the reactor and suspended in a premixed solution of methanol (91.2 kg, 6.0 vol) and acetic acid (5.03 kg, 0.25 vol). The slurry was stirred at 20° C. for 30 minutes. The reaction mixture was then heated to 50° C. and stirred for 1 hour. The slurry was cooled back to 20° C. and stirred for approximately 20 hours. A portion of the slurry was loaded onto Aurora filter A-26 and the solids left to settle for 1 hour. The filtration was then started, taking 75 minutes. The vessel and solids were washed with methanol (30.3 kg), taking 25 minutes. The filtered solids, containing the compound of formula (Ga), were optionally recycled to prepare a compound of formula (F) as set forth above in Example 3C. The filtrate was transferred into a new reactor through a 1-μm cartridge filter. The clear filtrate was held overnight at 22° C. Deionized water (15.4 kg, 0.8 vol) was then added over at least 20 minutes, giving crystal growth. After 1 hour, the remaining deionized water (49.9 kg, 2.6 vol) was added over at least 20 minutes. The reaction mixture was stirred for 2 hours and the solids isolated by filtration at 22° C. The reactor and solids were washed with a premixed solution of methanol (17.0 kg, 1.12 vol) and deionized water (9.22 kg, 0.48 vol). The solids were dried on the Aurora filter under vacuum at 45° C. Overall, 11.8 kg (58.0%) of (S)-3-hydroxymethyl-3-(6-tert-butyldimethylsilyloxy-1,3-benzodioxol-5-yl)-1-[[5-(trifluoromethyl)-2-furyl]methyl]indoline-2-one, a compound of formula (G), was isolated as a light tan solid. The chemical purity was 100.0 A % and chiral purity of 99.2% ee. An HPLC assay showed 99.9 wt % purity.

B. Alternatively, a 100-gallon reactor was charged with 3-(6-tert-butyldimethylsilyloxy-1,3-benzodioxol-5-yl)-1-[[5-(trifluoromethyl)-2-furyl]methyl]indoline-2-one (compound of formula (F), 20.0 kg, 37.7 mol), the catalyst, i.e., the compound of formula (Hb) (495 g, 0.832 mol), and paraformaldehyde (1.13 kg, 37.7 mol). n-Heptane (150 kg) was added by vacuum. A nitrogen sweep was established and the suspension stirred at 26° C. for 20 minutes. Aqueous formaldehyde (37% in H$_2$O, 3.98 kg, 49.0 mol) was added in one portion. The reaction was stirred at 26.0° C. for 47 hours, at which point 4.4 A % of 3-(6-tert-butyldimethylsilyloxy-1,3-benzodioxol-5-yl)-1-[[5-(trifluoromethyl)-2-furyl]methyl]indoline-2-one (compound of formula (F)) remained. The crude product was isolated at 26° C. The crude product was washed with n-heptane (20.6 kg). The solids were dried on a filter under vacuum at 45° C. for 40 hours to give 21.0 kg of crude (S)-3-hydroxymethyl-3-(6-tert-butyldimethylsilyloxy-1,3-benzodioxol-5-yl)-1-[[5-(trifluoromethyl)-2-furyl]methyl]indoline-2-one (compound of formula (G)). The crude product was charged back into the reactor and suspended in a premixed solution of methanol (94.5 kg) and acetic acid (5.25 kg). The slurry was stirred at 20° C. for 30 minutes. The reaction mixture was then heated to 62° C. and stirred for 1 hour. The slurry was cooled back to 20° C. and stirred for 4½ hours. The slurry was filtered to remove the solids. The solids, which contained the racemate of the compound of formula (G), were washed with methanol (31.6 kg) and optionally retained for use in Example 3C above. The combined filtrates were held overnight, then transferred into a new reactor through a 1-μm cartridge filter. DI water (16.1 kg) was then added to the filtrate over 20 minutes, giving crystal growth. After 1 hour, the remaining DI water (52.0 kg) was added over 20 minutes. The reaction mixture was stirred for 2 hours and the solids isolated by filtration at 22° C. The reactor and solids were washed with a premixed solution of methanol (17.7 kg) and DI water (9.65 kg). The solids were dried on the filter under vacuum at 45° C. for 41 hours to give 12.6 kg (59.5%) of the compound of formula (G) as a light tan solid with a purity of 98.6 A %, a chiral purity of 97.8% ee and a KF of 0.26%.

Example 7

Synthesis of Funapide

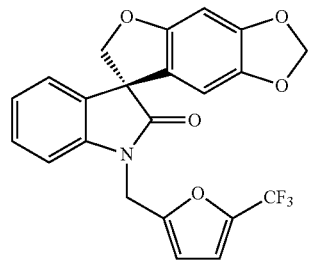 [SMILES: O=C1N(Cc2ccc(C(F)(F)F)o2)c2ccccc2[C@]12COc1cc3c(cc12)OCO3]

A. To a reactor was charged (S)-3-hydroxymethyl-3-(6-tert-butyldimethylsilyloxy-1,3-benzodioxol-5-yl)-1-[[5-(trifluoromethyl)-2-furyl]methyl]indoline-2-one (compound of formula (G), 10.7 kg, 19.0 mol, 1 equiv) acetonitrile (33.1 kg, 4 vol) and 47%-49% HBr in water (258 mL, 0.13 equiv). The reaction mixture was then heated to 37±3° C. over about 20 minutes. Upon reaching temperature, the reaction mixture was stirred for 6 hours. The reaction mixture was then cooled to 20±3° C. and extracted with cyclohexane (8.35 kg, 1 vol) to remove siloxane. Next chlorodiphenylphosphine (4.6 kg, 20.9 mol, 1.1 equiv) was added and the temperature raised to 37±3° C. The reaction mixture was agitated at this temperature for 21 h. An IPC test was performed and the remaining amount of the deprotected compound of formula (G') was measured to be 0.15 A % by HPLC. After cooling to 20±5° C., a solution 30% hydrogen peroxide in water (0.65 kg, 0.3 equiv) in acetonitrile (8.3 kg, 0.5 vol) was charged such that the temperature did not rise above 35° C. The reaction mixture was then cooled to 20±5° C. and an IPC test to measure peroxide showed none present. Next, the precipitated diphenylphosphinic acid was separated from the reaction mixture and washed with acetonitrile. The resulting solution containing the product was recharged to the reactor and solvent was exchanged for methanol. Once the solvent exchange was completed, the temperature of the reaction mixture was raised to 65±5° C. After cooling to 50±5° C., an additional amount of methanol (12 kg) was added to adjust the concentration to 163 mg/mL. The reaction mixture was cooled to 35±3° C. and seeds of the product, funapide, (110 g) were added. After agitating for 1 h, water (12.7 kg, 1.19 vol) was added maintaining the temperature at 35° C. The reaction mixture was then cooled to 22±3° C. over 30 minutes, agitated and kept at that temperature for 12.5 h. The product was then filtered and the cake was washed with a prepared 23% aqueous methanol solution (4 vol) followed by water (18 kg). The solids were agitated in the wash solvent while on the filter prior to application of vacuum. The solids were then dried under vacuum. The final weight was 6.59 kg of funapide (80.7%). IPC test for purity was measured at 99.6 A % with 100% ee as the chiral purity.

B. Alternatively, to a glass lined reactor was charged (S)-3-hydroxymethyl-3-(6-tert-butyldimethylsilyloxy-1,3-benzodioxol-5-yl)-1-[[5-(trifluoromethyl)-2-furyl]methyl] indoline-2-one (compound of formula (G), 12.5 kg, 22.3 mol, 1 eq.) acetonitrile (39.5 kg, 4 vol) and 47%-49% HBr in water (303 ml, 0.13 eq.). The reaction mixture was then heated to 37±3° C. over about 20 minutes. Upon reaching temperature, the reaction mixture was stirred for 6 hours. After this period an in-process test was performed with 0.2 A % by HPLC of the compound of formula (G') remaining. The reaction mixture was then cooled to 20±3° C. and held overnight. The next morning the solution was extracted with cyclohexane (9.75 kg, 1 vol) to remove siloxane. Next, an in-process test was performed for KF and the reaction mixture was found to contain 0.14% water. Chlorodiphenylphosphine (5.4 kg, 24.6 mol, 1.1 eq.) was then added and the temperature raised to 37±3° C. The reaction mixture was agitated at this temperature for 18 hours. An in-process test was performed and the remaining amount of the deprotected compound of formula (G) was measured to be 0.5 A % by HPLC. After cooling to 20±5° C. a solution 30% hydrogen peroxide in water (0.76 kg, 0.3 equiv) in acetonitrile (9.9 kg, 1.0 vol) was charged such that the temperature did not rise above 35° C. The reaction mixture was then cooled to 20±5° C. and an in-process test to measure peroxide showed no levels present. Next, using an Aurora filter, the precipitated diphenylphosphinic acid was separated from the reaction mixture. The collected solids were washed with acetonitrile (5.1 kg, 0.5 vol). The resulting solution containing the product was recharged to the reactor and solvent was exchanged for methanol. An in-process control showed 1.5 wt % acetonitrile detected by GC. Once the solvent exchange was completed, the temperature of the reaction mixture was raised to 65±5° C. and cooled to 50±5° C. where an in-process test was performed and showed the concentration was 137 mg/mL. This was within the acceptable range of 135-165 mg/mL. To begin the crystallization of the product, the reaction mixture was cooled to 35±3° C. and seeds of the product, funapide, (256 g, 0.3%) were added. After agitating for 1 hour, water (14.9 kg, 1.19 vol) was added maintaining the temperature at 35° C. The reaction mixture was then cooled to 22±3° C. over 30 min and agitated at that temperature for 15 hours. The product was then filtered using an Aurora filter and the cake was washed with a pre-prepared 23% aqueous methanol solution (4 vol) followed by water (22 kg). The solids were agitated in the wash solvent while on the filter prior to application of vacuum. The solids were then dried under vacuum (50-80 mm Hg) for 3.5 days. After that period, the product was found to have LOD of 0.2%. The final weight was 7.83 kg (82%). In-process test for purity was measured at 99.5 A % with 100% ee as the chiral purity.

Example 8

Further Purification of Funapide

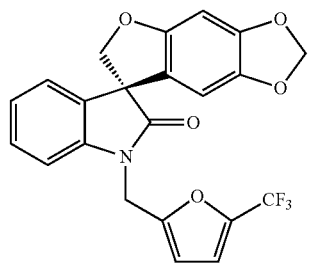 [SMILES: O=C1N(Cc2ccc(C(F)(F)F)o2)c2ccccc2[C@]12COc1cc3c(cc12)OCO3]

The numbers below correspond to the average of the two batches of this process (6.45 and 6.55 g of funapide, respectively).

To a reactor was charged funapide (6.5 kg, 15.1 moles), basic alumina (1.3 kg, 20 wt % of funapide) and methanol (32.5 kg, 6.2 vol). The reaction mixture was then heated to 65±3° C. followed by cooling to 55±3° C. The reactor contents were stirred at this temperature for at least 2 hours. Alumina was filtered hot using a sparkler filter. Methanol wash (5.15 kg, 1 vol) was charged to the reactor and taken through the sparkler and cartridge filter and combined with the rest of the solution. The contents of the portable tank were then transferred to a second reactor followed by a methanol rinse of the tank and the charge lines (about 2 kg). The second reactor contents were then heated to 65±5° C. and cooled to 35±3° C. over 30 minutes. Funapide seeds (65 g, 1%), in the polymorphic form known as Form $B_0$ (See FIG. 1), were then charged to the reactor and held for 1 hour at that temperature. Deionized water (20.2 kg, 3.1 vol) was charged over about 1 hour while maintaining the temperature at 35±3° C. The reaction mixture was then cooled to 22±3° C. over 30 minutes and held for at least an additional hour. The product was then filtered and the cake was washed with a prepared 30% aqueous methanol solution (17 kg, 3 vol) followed by water (about 19.7 kg, 3 vol). The solids were agitated in the wash solvent while on the filter prior to application of vacuum. The solids were then dried under vacuum at 70±5° C. The final weight was 6.2 kg (94.7% recovery) of funapide. An X-ray powder diffractogram of the funapide obtained by this process confirmed it to be the polymorphic form of funapide known as Form $B_0$ (see FIG. 1). IPC test for purity was measured at 99.8 A %. Material was next milled using a Fitz mill. Quality control results for assay on the two batches are 99.2 and 99.5% respectively and the chiral purity is 100% for both batches.

All of the U.S. patents, U.S. patent application publications, U.S. patent applications, PCT published patent applications, foreign patents, foreign patent applications and non-patent publications referred to in this specification are incorporated herein by reference in their entirety.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A method of preparing funapide having the following formula:

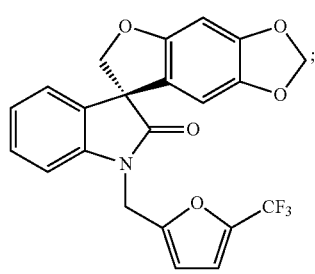 [SMILES: O=C1N(Cc2ccc(C(F)(F)F)o2)c2ccccc2[C@]12COc1cc3c(cc12)OCO3]

as the isolated (S)-enantiomer, or as a non-racemic mixture of enantiomers having an enantiomeric excess of the (S)-enantiomer over the corresponding (R)-enantiomer of greater than 94%;

wherein the method comprises treating a compound of formula (G):

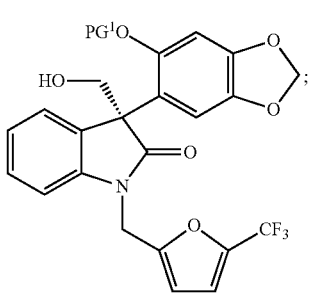

(G)

where PG¹ is an oxygen-protecting group, as an isolated (S)-enantiomer or a non-racemic mixture of enantiomers having an enantiomeric excess of the (S)-enantiomer over the corresponding (R)-enantiomer of greater than 94%, under suitable deprotection and intra-molecular cyclization conditions in the absence of an azodicarboxylate ester to provide funapide, as described above.

2. The method of claim 1, wherein the suitable intramolecular cyclization conditions comprise the use of a phosphine reagent.

3. The method of claim 2, wherein the phosphine reagent is chlorodiphenylphosphine.

4. The method of claim 1, wherein the suitable deprotection conditions comprise treating the compound of formula (G) in a polar aprotic solvent with an aqueous acid solution.

5. The method of claim 1, further comprising a C—C bond formation step prior to treating a compound of formula (G) under suitable intra-molecular cyclization conditions, wherein the C—C bond formation step comprises treating a compound of formula (F):

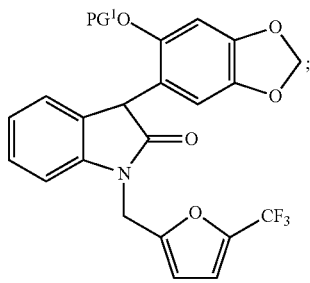

(F)

where PG¹ is as defined in claim 1 for the compounds of formula (G), with formaldehyde in the presence of a catalyst under suitable C—C bond formation conditions to provide the compound of formula (G), as an isolated (S)-enantiomer or a non-racemic mixture of enantiomers having an enantiomeric excess of the (S)-enantiomer over the corresponding (R)-enantiomer of greater than 94%, as described in claim 1.

6. The method of claim 5, wherein the catalyst is a thiourea-substituted quinine or hydroquinine compound.

7. The method of claim 6, wherein the catalyst is a compound of formula (H):

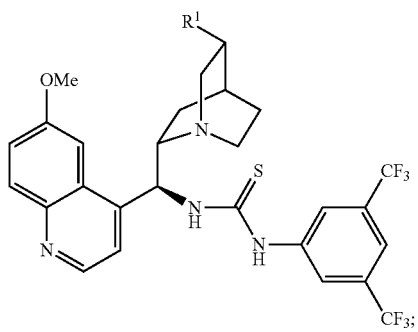

(H)

wherein R¹ is —CH₂—CH₃ or —CH=CH₂.

8. The method of claim 6, wherein the suitable C—C bond formation conditions comprise suspending the compound of formula (F) in an organic solvent and combining the suspension of the compound of formula (F) with an inorganic base.

9. The method of claim 5, further comprising a retro-aldol reaction step prior to treating the compound of formula (F) under suitable C—C bond formation conditions, wherein the optional retro-aldol reaction step comprises treating a compound of formula (Ga):

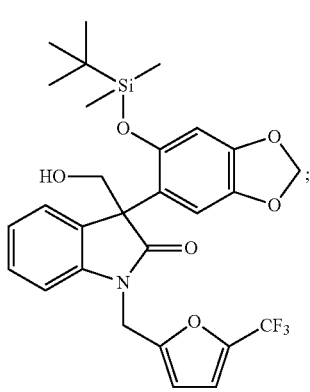

(Ga)

under suitable retro-aldol reaction conditions to provide a compound of formula (F), as described in claim 5.

10. The method of claim 5, further comprising an oxygen-protecting step prior to treating the compound of formula (F) under suitable C—C bond formation conditions, wherein the oxygen-protecting step comprises treating a compound of formula (E):

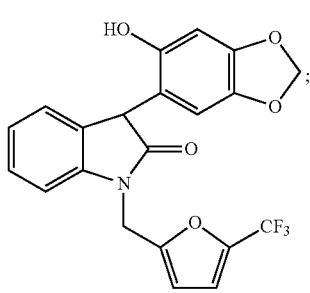

(E)

with a compound of formula PG¹X, where X is bromo, chloro or iodo and PG¹ is an oxygen-protecting group under suitable oxygen-protecting conditions to provide a compound of formula (F), as described in claim 5.

11. The method of claim 10, wherein the suitable oxygen-protecting conditions comprise treating the compound of formula (E) with an oxygen-protecting group provider in an polar aprotic solvent in the presence of a base.

12. The method of claim 10, further comprising a dehydroxylation step prior to treating the compound of formula (E) under suitable oxygen-protecting conditions, wherein the dehydroxylation step comprises treating a compound of formula (D):

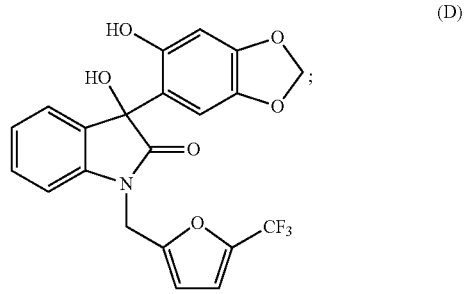 [SMILES: O=C1N(Cc2ccc(C(F)(F)F)o2)c2ccccc2C1(O)c1cc2c(cc1O)OCO2]

under suitable dehydroxylation conditions to provide a compound of formula (E), as described in claim 10.

13. The method of claim 12, wherein the suitable dehydroxylation conditions comprise acid-promoted dehydroxylation of the compound of formula (D) followed by reduction with an appropriate silane or siloxane.

14. The method of claim 12, further comprising a coupling step prior to treating a compound of formula (D) under suitable dehydroxylation conditions, wherein the coupling step comprises:
(a) treating a compound of formula (A):

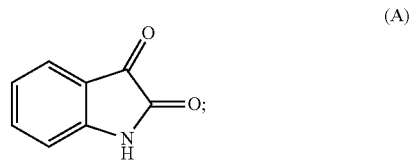

with a compound of formula (B):

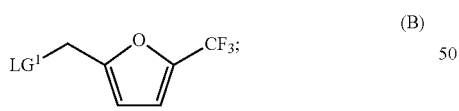

where $LG^1$ is a leaving group, under suitable N-alkylation conditions to form a reaction mixture, and
(b) adding to the reaction mixture a compound of formula (C):

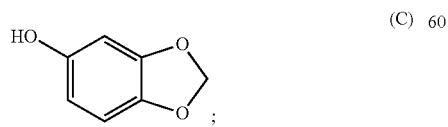

under suitable coupling conditions to provide a compound of formula (D), as described in claim 12.

15. The method of claim 14, wherein the compound of formula (D) is isolated from the reaction mixture by crystallization under suitable crystallization conditions.

16. The method of claim 14, wherein the suitable N-alkylation conditions comprise reductive amination conditions in the presence of an aldehyde and a reducing agent.

17. The method of claim 14, wherein the suitable coupling conditions comprise treating the compound of formula (C) with the reaction mixture to form the compound of formula (D) in the absence of a Grignard reagent.

18. A method of preparing funapide having the following formula:

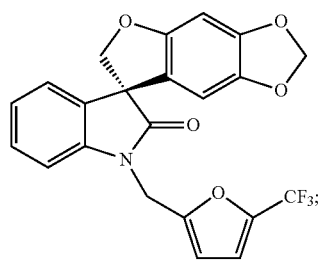 [SMILES: O=C1N(Cc2ccc(C(F)(F)F)o2)c2ccccc2[C@]12COc1cc3c(cc12)OCO3]

as the isolated (S)-enantiomer substantially free from the corresponding (R)-enantiomer, or as a non-racemic mixture of enantiomers having an enantiomeric excess of the (S)-enantiomer over the corresponding (R)-enantiomer of greater than 94%;

wherein the method comprises:
(1) a coupling step comprising:
(a) treating a compound of formula (A):

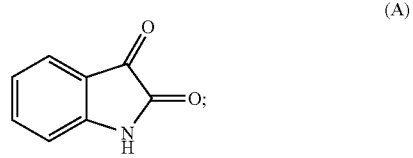 [SMILES: O=C1Nc2ccccc2C1=O]

with a compound of formula (B):

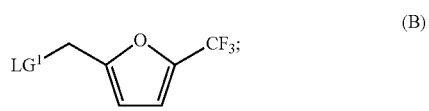

where $LG^1$ is a leaving group, under suitable N-alkylation conditions to form a reaction mixture, and
(b) adding to the reaction mixture a compound of formula (C):

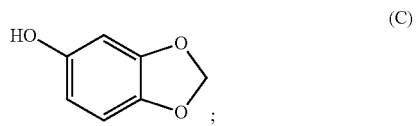

under suitable coupling conditions to provide a compound of formula (D):

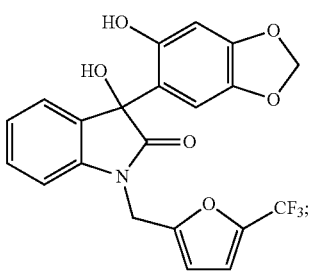

which is isolated from the reaction mixture by standard isolation techniques;

(2) a dehydroxylation step comprising treating the compound of formula (D) under suitable dehydroxylation conditions to provide a compound of formula (E):

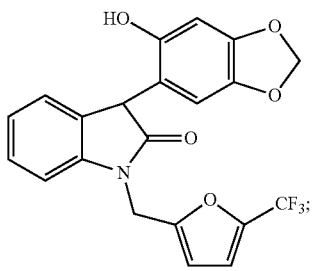

(3) an oxygen-protecting step comprising treating the compound of formula (E) with a compound of formula $PG^1X$, where X is bromo, chloro or iodo and $PG^1$ is an oxygen-protecting group under suitable protecting conditions to provide a compound of formula (F):

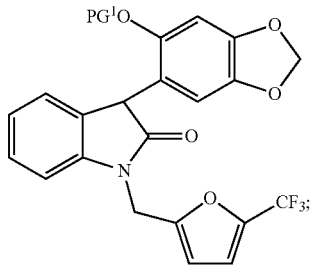

where $PG^1$ is an oxygen-protecting group;

(4) a C—C bond formation step comprising treating the compound of formula (F) with formaldehyde in the presence of a catalyst under suitable C—C bond formation conditions to provide a compound of formula (G):

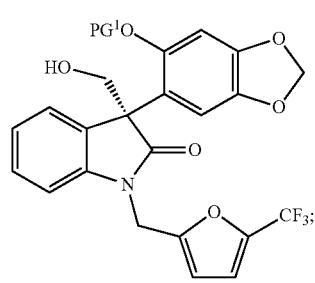

where $PG^1$ is an oxygen-protecting group, as an isolated (S)-enantiomer or a non-racemic mixture of enantiomers having an enantiomeric excess of the (S)-enantiomer over the corresponding (R)-enantiomer of greater than 95%;

(5) an intramolecular cyclization step comprising treating the compound of formula (G), as an isolated (S)-enantiomer or a non-racemic mixture of enantiomers having an enantiomeric excess of the (S)-enantiomer over the corresponding (R)-enantiomer of greater than 95%, under suitable intramolecular cyclization conditions in the absence of an azodicarboxylate ester to provide funapide, as an isolated (S)-enantiomer or a non-racemic mixture of enantiomers having an enantiomeric excess of the (S)-enantiomer over the corresponding (R)-enantiomer of greater than 95%;

(6) optionally, a purification step comprising treating funapide under suitable purification conditions to provide a higher yield of funapide than achieved in step (5) above.

* * * * *